US008420396B2

(12) United States Patent
Uhlmann et al.

(10) Patent No.: US 8,420,396 B2
(45) Date of Patent: Apr. 16, 2013

(54) CONJUGATES AND PROCESSES FOR THEIR PREPARATION AND THEIR USE FOR TRANSPORTING MOLECULES ACROSS BIOLOGICAL MEMBRANES

(75) Inventors: Eugene Uhlmann, Glashuetten (DE); Beate Greiner, Leiderbach (DE); Eberhard Unger, Jena-Cospeda (DE); Gislinde Gothe, Jena-Cospeda (DE); Marc Schwerdel, Jena (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 723 days.

(21) Appl. No.: 11/622,156

(22) Filed: Jan. 11, 2007

(65) Prior Publication Data
US 2008/0071069 A1 Mar. 20, 2008

Related U.S. Application Data

(63) Continuation of application No. 09/627,787, filed on Jul. 27, 2000, now abandoned.

(30) Foreign Application Priority Data

Jul. 28, 1999 (DE) .................................. 199 35 302

(51) Int. Cl.
 C12N 15/00 (2006.01)
 C12N 5/00 (2006.01)
(52) U.S. Cl.
 USPC ........................... 435/455; 435/325; 435/375
(58) Field of Classification Search .................. None
 See application file for complete search history.

(56) References Cited

U.S. PATENT DOCUMENTS

| | | | |
|---|---|---|---|
| 5,405,746 A | 4/1995 | Uhlen | |
| 5,698,411 A | 12/1997 | Lucas et al. | |
| 5,763,208 A * | 6/1998 | Bischofberger et al. | 435/40.5 |
| 5,820,873 A | 10/1998 | Choi et al. | |
| 6,013,639 A | 1/2000 | Peyman et al. | |
| 6,033,909 A | 3/2000 | Uhlmann et al. | |
| 6,080,580 A | 6/2000 | Baker et al. | |
| 6,184,379 B1 | 2/2001 | Josel et al. | |
| 6,228,982 B1 | 5/2001 | Norden et al. | |
| 6,335,434 B1 | 1/2002 | Guzaev et al. | |

FOREIGN PATENT DOCUMENTS

| | | |
|---|---|---|
| CA | 2339967 | 2/2000 |
| CA | 2377267 | 12/2000 |
| EP | 0552766 A2 | 7/1993 |
| EP | 0962497 A1 | 12/1999 |
| WO | WO 99/55383 | 11/1994 |
| WO | WO 95/06659 | 3/1995 |

OTHER PUBLICATIONS

Limberg et al (Liebigs Ann. 11:1773-1784, 1996).*
Chen et al., New Fluorescent Probes for Protein Kinase C, J. of Bio Chem., vol. 268, No. 21, Jul. 25, 1993.
Cohen et al., Carbonic Anhydrase Catalysed Hydrolysis of Fluorgenic Esterase Substrates, Phytochemical Analysis, vol. 2, 1991, pp. 60-64.
F. Abe, Hydrostatic Pressure Enhances Vital Staining with Carboxyfluorescein or Carboxydichlorofluorescein in *Sassharomyes cerevisiase*: Efficient Detection of Labeled Yeasts by Flow Cytometry, Applied and Environmental Microbiology, vol. 64, No. 3, Mar. 1998, pp. 1139-1142.
Laurent et al., Esterase-Triggered Fluorescence fo Fluorogenic Oligonucleotides, Bionconjugate Chem., vol. 8, 1997, pp. 856-861.
Limberg et al., A New Assay for Sialystransferases Using Fluorescein-Labelled Acceptors, Liebigs Ann. 1996, pp. 1773-1784.
Ohsako et al., Modeling of Controlled Release of Aspirin Derivatives from Human Erythrocytes, Bio. Pharm. Bull. vol. 18, No. 2, 1995, pp. 310-314.
S.H. Chen et al., New Thermotropic Chiral Nematic Copolymers Using (1S,2S,3S,5R)-(+)- and (1R,2R,3R,5S)-(−) Isopinocampheol as Building Blocks, Macrocmolecules, vol. 23, 1990, pp. 5055-5058.
Takeuchi et al., Effect of Nitric Oxide-Releasing Aspirin Derivative on Gestic Functional and Ulcerogenic Responses in Rats: Comparison with Plain Aspirin, J. of Pharmacology and Experimental Therapetuics. vol. 286, No. 1, 1998, pp. 115-121.
Williams at al., Kinetics of the Polymerization of 4-Acetoxybenzoic Acid and 6-Acetoxy-2-naphthoic Acid, Macromolecules, vol. 29, 1996, pp. 1874-1879.
Tanaka et al., EWS-Fli1 antisense oligodeoxynucleotide inhibits proliferation of human Ewing's sarcoma and primitive neuroectodermal tumor cells, J. Clin. Invest., vol. 99, No. 2, 1997, pp. 239-247.
White et al, Inhibition of the multiple antibiotic resistance (mar) operon in *Escherichia coli* by antisense DNA analogs, Antimicrob. Agents and Chemother vol. 41, No. 12, 1997, pp. 2699-2704.
Akhtar et al., Anti-HIV therapy with antisense oligonucleotides and ribozymes: realistic approaches or expensive myths?, Journal of Anitimicrobial Chemotherapy, vol. 38, 1996, pp. 159-165.
Gryaznov et al., Oligonucleotide N3—P5' phosphoramidates as potential therapeutic agents, Biochmica at Biophysica Acta, vol. 1489, 1999, pp. 131-140.
Ruschkowski et al., Pretargeting Using Peptide Nucleic Acid, 1997, Supp. to Cancer, pp. 2699-2705.
Mardirossian et al., In Vivo Hybridization of Technetium-99m-Labeled Peptide Nucleic Acid (PNA), J. Nucl. Med, vol. 38, 1997, pp. 907-913.
Stedman's Medical Dictionary, 26th Edition, 522, 1340, 1341, 1995.
Crooke at al., Antisense Oligonucleotides in the Context of Modern Molecular Drug Discovery and Development, Antisense Research and Application 1993, pp. 8-35.
Branch, A good antisense molecule is hard to find TIBS, 1998, pp. 45-50.
Ho et al., Antisense Oligonucleotides as Therapeutics for Malignant Diseases, Seminars in Oricology, 1997, vol. 24, No. 2, pp. 187-202.

(Continued)

*Primary Examiner* — Janet Epps-Smith
(74) *Attorney, Agent, or Firm* — Nicole L. M. Parson

(57) ABSTRACT

The present invention provides conjugates, processes for their preparation, and the use of these conjugates for transporting low-molecular-weight compounds and macromolecules across biological membranes, in particular for transporting molecules into cells. The present invention also provides pharmaceutical compositions, diagnostic aids, and test kits in which these conjugates are present or used.

8 Claims, 10 Drawing Sheets

OTHER PUBLICATIONS

Cole-Strauss et al., Correction of the Mutation Responsible for Sickle Cell Anemia by an RNA-DNA Oligonucleotide, Science, vol. 273, 1996, pp. 1386-1389.

Norton et al, Inhibition of human telomerase activity in peptide nucleic acids, Nature Biotechnology, vol. 14, 1996, p. 615-619.

Bennett et al., Caitionic Lipids Enhance Cellular Uptake and Activiy of Phosphorothioate Antisense Oligonucleotides, Molecular Pharmacology, vol. 41, 1992, pp. 1023-1033.

Breeuwer et al., Characterization of Uptake and Hydrolysis of Fluorescein Diacetate and Carboxyfluorescein Diacetate by Intracellular Esterases in *Saccharomyces cerevisiae*, Which Result in Accumulation of Fluorescent Product, Applied and Evironmental Microbiology, vol. 61, No. 4, 1995, pp. 1614-1619.

Iyer et al., Bioreversible Oligonucleotide Conjugates by Site-Specific Derivatization, Biorganic & Medicinal Chemistry Letters, vol. 7, No. 7, 1997, pp. 871-876.

Kielkopf et al., A Structural Basis for Recognition of A T and T A Base Pairs in the Minor Grove of B-DNA, Science, vol. 282, 1998, pp. 111-115.

Uhlmann et al., Antisense Oligonucleotides: A New Therapeutic Principle, Chemical Reviews, vol. 90, No. 4, 1990, pp. 544-584.

Hunziker et al., Nucleic Acid Analogues: Synthesis and Properties, Modern Synthetic Methods, Ed. Beat Erst et al., Verlag Helvetica Chimica Acta, Basel, 1995, pp. 333-417.

Stirchak t al., Uncharged stereoregular nucleic acid analogs: 2. Morpholino nucleoside oligomers with carbamate internucleoside linkages, Nucleic Acids Research, vol. 17, No. 15, 1989, pp. 6129-6141.

Summerston et al., Morpholino Antisense Oligomers: Design, Preparation and Properties. Antisense & Nucleic Acid Drug Development, vol. 7, 1997, pp. 187-195.

Nielsen et al., Peptide Nucleic Acid (PNA). A DNA Mimic with a Peptide Backbone, Bioconjugate Chem., vol. 5, 1994, pp. 3-7.

Peyman et al., Phosphonic Ester Nucleic Acids (PHONAs): Oligonucleotide Analogues with an Achiral Phosphonic Acid Ester Backbone, Agnew Chem. Int. Ed. Engl. vol. 35, No. 22, 1996, pp. 2636-2638.

Singh et al., LNA (locked nucleic acids): synthesis and high-affinity nucleic acid recognition, Chem. Commun. 1998, pp. 455-456.

Singh et al., Universality of LNA-mediated high affinity nucleic acid recognition, Chem. Commun. 1998, pp. 1247-1248.

Froehler et al., Triple-Helix Formation by Oligodeoxynucleotides Containing the Carbocyclic Analogs of Thymidine and 5-Methyl-2'-deoxycytidine, J. Am. Chem. Soc. vol. 114, 1992, pp. 8320-8322.

Vandendriessche et al., Acyclic Oligonucleotides: Possibilities and Limitations, Tetrahedron. vol. 49. No. 33, 1993, pp. 7223-7238.

Tarkoy et al., Nucleic-Acid Analogues with Constraint Conformational Flexibility in the Sugar-Phosphate Backbone ('Bicyclo-DNA'), Helvetica Chemica Acta, vol. 76, 1993, pp. 481-510.

Manoharan, M., Designer Antisense Oligonucleotides: Conjugation Chemistry and Functional Placement. Chapter 17, Antisense Research and Applications, Eds., B. Leblew et al., 1993, pp. 303-349.

Koga et al., Alternating alpha, Beta-Oligothymidylates with Aternating (3'-3')- and (5'-5')-Internucleotidic Phosphodiester Linkages as Models for Antisense Oligodeoxyribonucleotides, J. of Organic Chem., vol. 56, No. 12, 1991, pp. 3757-3763.

Goodchild, J., Conjugates of Oligonucleotides and Modified Oligonucleotides: A Review of Their Synthesis and Properties, Bioconjugate Chemistry, vol. 1. No. 3, 1990, pp. 165-186.

Beaucage et al., The Functionalization of Oligonucleotides Via Phosphoramidite Derivatives, Tetrahedron, vol. 49, No. 10, 1993, pp. 1925-1963.

Weiner et al., Liposomes as a Drug Delivery System, Drug Development and Industrial Pharmacy, vol. 15, No. 10, 1989, pp. 1523-1554.

Hayashi et at., In vivo transfer of gene and oligodeoxynucleotides into skin of fetal rats by incubation in amniotic fluid, Gene Therapy, vol. 3, 1995, pp. 878-885.

Sawadogo et al., A rapid method for the purification of deprotected oligodeoxynucleotides, Nucleic Acids Research, vol. 19, No. 3, 1991, pp. 674.

Starke et al., Bile Acid-Oligodeoxynucleoside Conjugates: Synthesis and Liver Exertion in Rats, Bioorganic & Medicinal Chemistry Letters, vol. 11, 2001, pp. 945-949.

Whittemore et al., Synthesis and Electrochemistry of Anthraquinone-Oligodeoxynucleotide Conjugates, Bioconjugate Chem. vol. 10, 1999, pp. 261-270.

Luehrsen et al., High-density Hapten Labeling and HRP Conjucation fo Oligonucleotides for Use as in Situ Hybridization Probes to Detect mRNA Targets in Cells and Tissues, The J. of Histochemistry & Cytochemistry vol. 48, No. 1, 2000, pp. 133-145.

Rait et al., 3'-End Conjugates of Minimally Phosphorothioate-Protected Oligonucleotides with 1-O-Hexadecylglycerol: Synthesis and Anti-ras Activity in Radiation Resistant Cells, Bioconjugate Chem., vol. 11, No. 2, 2000, pp. 153-160.

Manoharan, M., 2'-Carbohydrate modifications in antisense oligonucleotide therapy: Importance of conformation, configuration and conjugation, Biochimica of Biophysica Acta vol. 1489, 1999, pp. 117-130.

Prakash et al., 2'-O-{2-[N,N-(Dialkyl)aminooxylethyl}-Modifified Antisense Oligonucleotides, Organic Letters. vol. 2, No. 25, 2000, pp. 3995-3998.

Iyer at al., Stereospecific bio-reversibility of dinucleoside S-alkyl phosphorothiolates to dinucleoside phosphorothioates, Bioorg. Med. Chem. Letters, vol. 4, No. 20, 1994, pp. 2471-2476.

Iyer et al., Acyloxyaryl prodrugs of oligonucleoside phosphorothioates, Bioorg. Med. Chem. Letters, vol. 6, No. 16, 1996, pp. 1917-1922.

Higgins et al., Antisense Inhibition of the p65 Subunit of NF-B Blocks Tumorigenicity and Causes Tumor Regression, PNAS, vol. 90, 1993, pp. 9901-9905.

Yamamoto et al., Strand-Specificity in the Transformation of Yeast with Synthetic Oligonucleotides, Genetics vol. 131, No. 4, 1992, p. 811-819.

Maeda et al., Investigation of Factors Involved in the Uptake Velocity of Fluorescein Diacetate and Intracellular Fluorescence Polarization Value. II. Cytotoxicity Produced by Anticancer AgentS, Cell Structure and Function, vol. 7, 1982, pp. 177-182.

International Search Report WO01/08707 A3 dated Feb. 8, 2001.

\* cited by examiner (F6)

(F7)

"F8"

"F9"

(F10)

(F11)

SEQUENCE LISTING

<160> NUMBER OF SEQ ID NOS: 63

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:
       oligonucleotide

```
<400> SEQUENCE: 1
gcgacgccat gacgg                                              15

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
cgacgccatg ac                                                 12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
atgacggaat tc                                                 12

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
tattccgtca t                                                  11

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
aaaaaaaaaa aaaaaaaaaa                                         20

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
aaaaaaaaaa aaaaaaaaaa aaaaaaaaaa aaaaaaaaaa aaaaaaaaaa        50

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence:
      oligonucleotide
```

-continued

<400> SEQUENCE: 7
aaaaaaaaaa aaaaaaaaaa aaaaaaaaaa aaaaaaaaaa aaaaaaaaaa aaaaaaaaaa    60
aaaaaaaaaa aaaaaaaaaa                                                 80

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ttccatggtg gc                                                         12

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttcactgtgg gc                                                         12

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tggcgccggg cc                                                         12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tgccggccgg gc                                                         12

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gcgtttgctc ttcttcttgc g                                               21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide -continued

<400> SEQUENCE: 13
acacccaatt ctgaaaatgg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
aggtccctgt tcgggcgcca                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gcggggctcc atgggggtcg                                              20

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
cagctgcaac ccagc                                                   15

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
tattccgtca t                                                       11

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ttccgtcatc gctcctcagg gg                                           22

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 19
ggctgccatg gtccc                                                        15

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ggctgctgga gcggggcaca c                                                 21

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
aacgttgagg ggcat                                                        15

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gtgccggggt cttcgggc                                                     18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
cgagaacatc atcgtgg                                                      17

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ggagaacatc atggtcgaaa g                                                 21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 25
cccgagaaca tcatggtcga ag                                              22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
ggggaaagcc cggcaagggg                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
cacccgcctt ggcctcccac                                                 20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
gggactccgg cgcagcgc                                                   18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
ggcaaacttt cttttcctcc                                                 20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
gggaaggagg aggatgagg                                                  19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 31
ggcagtcatc cagcttcgga g                                         21

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
tctcccagcg tgcgccat                                             18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
gcgctgatag acatccatg                                            19

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ggaggcccga cc                                                   12

<210> SEQ ID NO 35
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
ggtttcggag gc                                                   12

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
tggtggaggt ag                                                   12

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 37
gcatggtgga gg                                                            12

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
ttggcatggt gg                                                            12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
gcctgggacc ac                                                            12

<210> SEQ ID NO 40
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
cagcctggga cc                                                            12

<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
tgcagcctgg ga                                                            12

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gtgcagcctg gg                                                            12

<210> SEQ ID NO 43
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
```

-continued

```
<400> SEQUENCE: 43
ggtgcagcct gg                                                         12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
atgggtgcag cc                                                         12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
ggcttgaaga tg                                                         12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46 gcagccccog ca                                                         12

<210> SEQ ID NO 47
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
gcagcagccc cc                                                         12

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
tcccgcctgt gacatgcatt                                                 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 49
gttctcgctg gtgagtttca                                              20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
gcgtgcctcc tcactggc                                                18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
gcagtaagca tccatatc                                                18

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
gcccaagctg gcatccgtca                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 53
cccccaccac ttccctctc                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 54
ctcccccacc acttcccctc                                              20

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 55
gctgggagcc atagcgagg                                           19

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
actgctgcct cttgtctcag g                                        21

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 57
caatcaatga cttcaagagt tc                                       22

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58
gcggcggaaa agccatcg                                            18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
gtgtcggggt ctccgggc                                            18

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 60
cacgttgagg ggcat                                               15

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:
      oligonucleotide
```

```
-continued

<400> SEQUENCE: 61
gtcttccata gttactca                                                   18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 62
gatcaggcgt gcctcaaa                                                   18

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 63
gatggagggc ggcatggcgg g                                               21
```

CONJUGATES AND PROCESSES FOR THEIR PREPARATION AND THEIR USE FOR TRANSPORTING MOLECULES ACROSS BIOLOGICAL MEMBRANES

FIELD OF THE INVENTION

The present invention provides conjugates, processes for their preparation and the use of these conjugates for transporting low-molecular-weight compounds and macromolecules across biological membranes, in particular for transporting molecules into cells. The present invention also provides medicaments and diagnostic aids and test kits in which these conjugates are present or used.

BACKGROUND OF THE INVENTION

Frequently, a limiting factor for the therapeutic utilization of molecules whose target is within the cell is their unsatisfactory cellular uptake and unfavorable intracellular distribution. Typical examples are macromolecules such as nucleic acids, which bind in sequence-specific manner to cellular DNA or RNA, thus inhibiting gene expression. Antisense oligonucleotides are short single-stranded nucleic acids, which bind via Watson-Crick base pairs to complementary mRNA, inhibiting its translation into the corresponding protein. Triplex-forming oligonucleotides bind via so-called "Hoogsteen base pairing" to the deep groove of the DNA double helix forming a triple helix, thus inhibiting the transcription of the genes in a sequence-specific manner. Other intracellularly acting oligonucleotides are, for example, the so-called "decoy" oligonucleotides which mimic the binding regions for transcription factors. By treatment with decoy oligonucleotides, certain transcription factors can be intercepted in a sequence-specific manner, thus inhibiting activation of the transcription. A further group of intracellularly acting oligonucleotides, the chimera plasts, is used for targeted gene correction (Cole-Strauss et al., *Science* 273:1386-1389 (1996)). For this gene correction, too, the uptake of the chimera plast oligonucleotide into the cell is essential. Examples of further intracellularly acting nucleic acids are those which interact with cellular enzymes, in particular with telomerases (Norton et al. *Nat. Biotechn.* 14:615 (1996)). A further class of nucleic acids, preferably double-stranded DNA, can code for certain proteins, which are expressed intracellularly in the sense of gene therapy.

For example, the uptake of an oligonucleotide in vitro into a cell, for example by simple addition of the oligonucleotide to the cell culture medium, is a relatively inefficient process, because only a small fraction of the added oligonucleotide is actually taken up into the cell. The uptake process takes many hours, and in most cases, a plateau phase is reached only after 8 to 16 hours. It is assumed that the oligonucleotides are taken up in an endocytosis-like process. However, a general problem with uptake via endocytosis is that a large proportion of the oligonucleotides present are not free in the cytoplasm, but enclosed in certain cell structures, i.e., the lysosomes and endosomes. In the case of fluorescently labeled oligonucleotides, this localized distribution can indeed be observed by fluorescence microscopy. Owing to this vesicular localization, the concentration of free oligonucleotide, which is actually available for hybridization to the mRNA, is considerably reduced. Moreover, depending on the cell type and the conditions present, only a certain fraction of cells take up the oligonucleotide in the first place. Therefore, for the efficient use of antisense oligonucleotides, mixtures with penetration enhancers, such as, for example, cationic lipids (Bennett et al., *Mol. Pharmacol.* 41:1023 (1992)) are generally employed.

It was an object of the present invention to improve cellular uptake of molecules, in particular of macromolecules, such as, for example, oligonucleotides.

Examination of cellular uptake of oligonucleotides is generally carried out using either radioactively labeled or fluorescently labeled oligonucleotides. Fluorescence labeling of an oligonucleotide is carried out, for example, by reacting the amino function of an oligonucleotide with fluorescein isothiocyanate (FITC). The fluorescein can be introduced, for example, into the 3' end of an oligonucleotide via a commercially available fluorescein-derivatized solid-phase support, or into the 5' end via a commercially available fluorescein phosphitylating reagent. In all cases, the oligonucleotide-bound fluorescein is, owing to the carboxylic acid function, present as a negatively charged structural element, which is strongly fluorescent.

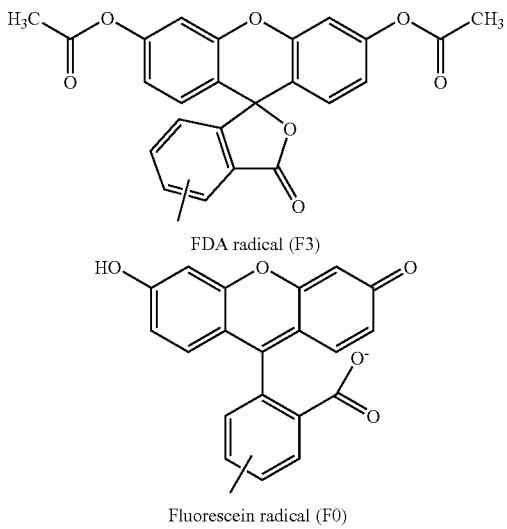

FDA radical (F3)

Fluorescein radical (F0)

In contrast to fluorescein, fluorescein diacetate (FDA) is a neutral vital dye, which is transformed into the fluorescent fluorescein only after removal of the two ester groups and opening of the lactone ring, but which is not fluorescent in the form of the lactone.

It is known that FDA (hereinbelow also referred to as "F3"), as a neutral, non-fluorescent molecule, is taken up by living cells via passive diffusion and is cleaved intracellularly by esterases to give the fluorescent fluorescein (Breeuwer et al., *Appl. Environ. Microbiol.* 61:1614 (1995); Maeda et al., *Cell Struct. Funct.* 7:177 (1982)). Hitherto, the only FDA derivatives described have been those containing an amine-reactive group, such as, for example, isothiocyanate; these FDA derivatives are used for staining intracellular proteins or cell components. Neither conjugates of FDA with other molecules nor FDA-labeled oligonucleotides (conjugates of FDA and oligonucleotide) have been described-previously.

In the cytoplasm, FDA is cleaved by esterases. Accordingly, it is possible to determine, by FDA labeling of an oligonucleotide, the proportion of "free" oligonucleotide, i.e., how much oligonucleotide is present in the cytoplasm and available for hybridization—in relation to the proportion of oligonucleotide present in vesicles ("captured" oligonucleotide)—and accordingly not available for hybridization. Owing to the high total number of negative charges in an oligonucleotide and the fact that FDA-labeled and fluorescein-labeled oligonucleotides (in the case where the oligonucleotide is identical) differ by only one net charge, one would expect that FDA-labeled and fluorescein-labeled oligonucleotides would exhibit very similar cellular uptake and distribution.

However, surprisingly, it has been found that FDA-labeled and fluorescein-labeled oligonucleotides differ considerably in their uptake into cells, i.e., in duration and efficiency of the uptake of the oligonucleotides as well as in cellular localization of the oligonucleotides that have been taken up. Cells take up FDA-labeled oligonucleotide much more rapidly than the corresponding fluorescein labeled oligonucleotide. FDA-labeled oligonucleotides can, after simple incubation, for example with human cells, be detected intracellularly after only five minutes, whereas, the uptake of radioactively labeled and fluorescein-labeled oligonucleotides requires several hours. It is also surprising that the FDA-labeled oligonucleotides are taken up into virtually any cells (>90% of cells). Whereas, the rate of uptake in the methods hitherto described for transferring oligonucleotides or polynucleotides into cells is generally considerably lower; in the latter case, frequently only about 30 to 60% of the cells are loaded with oligonucleotides. Another advantage is the intracellular distribution of the FDA-labeled oligonucleotides, which is much more uniform. This more uniform distribution indicates that the oligonucleotides are not—as described above—mainly enclosed in vesicles (for example, endosomes, lysosomes), but distributed in the entire cell—i.e., in the cytosol and the nucleus. This is an indication that a large fraction of "free" oligonucleotide is present. Only these "free" oligonucleotides are available for binding to the target (target molecule, target nucleic acid) or as active compound. Another advantage is the fact that no damage to the cells is observed when FDA-labeled oligonucleotides are used; in contrast, the use of lipocationic penetration enhancers frequently results in damage of the cell membrane. As a consequence of these unexpected properties, the FDA-labeled oligonucleotides have, compared to the methods hitherto described for introducing oligonucleotides or polynucleotides into cells, the decisive advantage that they can be introduced into the cells more effectively, where they are also more readily available. Owing to this, the FDA-labeled oligonucleotides have a considerably improved biological activity. Because of the improved biological activity, less oligonucleotide has to be used. Owing to this and the fact that a FDA-labeled oligonucleotide is taken up more effectively—both with respect to the amount and to time—into a cell, (toxic) side effects are reduced.

Surprisingly, it has been found that these advantageous properties are not limited to FDA-labeled oligonucleotides. Virtually any molecule can be introduced effectively into a cell or transported across a biological membrane with the aid of FDA-labeling—i.e., by coupling a molecule to be transported to FDA, or conjugating it ("FDA conjugate"). Furthermore, it has been found that this principle is not limited to FDA conjugates, but also applies to all aryl ester conjugates of a certain chemical structure. Thus, the present invention is a novel principle for transporting molecules across biological membranes. Since these compounds have hitherto, except for one exception, not been described in the prior art, the corresponding conjugates—a molecule to be transported coupled to or conjugated with an aryl ester of a certain chemical structure—likewise form part of the subject matter of the present invention. These conjugates cannot be prepared by known processes. The present invention, therefore, also provides a process for preparing the conjugates.

Bioreversible O-acylaryl conjugates, which have been proposed as prodrugs of oligonucleotides (Iyer et al., *Bioorganic & Med. Chem. Lett.* 7: 871-876 (1997)), are known. The chemical structure of these compounds is—in the case that the aryl radical is an aromatic 6-membered ring—similar to that of the conjugates according to the invention. However, in the bioreversible O-acylaryl conjugates, the hydrolysis of the ester results in a destabilization of the bond between the aryl radical and the phosphotriester of the oligonucleotide, so that the bioreversible O-acylaryl conjugate is cleaved into its components, i.e., the free oligonucleotide and the O-acylaryl radical. This prodrug concept serves to mask the negative charge of the internucleotide phosphate bridge and thus, to facilitate uptake of the oligonucleotide into the cell. However, in contrast to the conjugates according to the invention, no accelerated uptake of the oligonucleotides into the cells and likewise no changed intracellular distribution of the oligonucleotides have been found for these prodrugs. Furthermore, an uptake of the oligonucleotides into other organisms has not been reported. In contrast, in the conjugates according to the invention, the covalent bond between the aryl radical and the oligonucleotide is preserved during uptake into the cell. The preservation of the covalent bond between aryl radical and oligonucleotide can easily be determined by fluorescence microscopy, if the aromatic unit is only fluorescent after cleavage of the ester, such as, for example, in the case of FDA.

SUMMARY OF THE INVENTION

The present invention provides a conjugate which comprises at least one molecule to be transported and at least one aryl radical of the formula I,

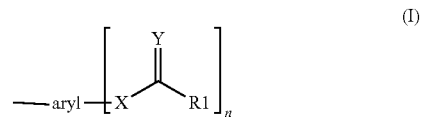

(I)

wherein
aryl is a group that contains at least one ring having aromatic character;
X is O or N; preferably X=O;
Y is O, S or NH—$R^2$; preferably Y=O;
$R^1$ is a substituted or unsubstituted $C_1$-$C_{23}$ alkyl radical, which may be straight-chain or branched and may contain double and/or triple bonds; for example an arylalkyl radical;
$R^2$ is a substituted or unsubstituted $C_1$-$C_{18}$ alkyl radical which may be straight-chain or branched and may contain double and/or triple bonds; and
n is an integer greater than or equal to 1,
where the aryl radical is attached to the molecule to be transported either directly via a chemical bond or indirectly via a chemical group, where the chemical group is not a $CH_2$—S group, if the attachment is through an internucleotide phosphodiester bond of the molecule to be transported.

BRIEF DESCRIPTION OF THE FIGURES

FIG. 3 shows different examples (A, B, C, D, E, F, G) of a conjugation between a molecule to be transported (here an oligonucleotide) and aryl radicals of the formula (I). "R" is a radical of the formula (I); "B" is a heterocyclic base.

FIG. 4 shows a possibility of preparing a conjugate according to the invention (here consisting of FDA-isothiocyanate and oligonucleotide).

FIG. 5 shows the uptake of the conjugate CO_5 into REH cells from the medium over time, where in one case medium without serum (♦) and in another case medium with serum (■) were used. The uptake into the cell was determined with the aid of FACS.

DETAILED DESCRIPTION OF THE INVENTION

Figure 1:
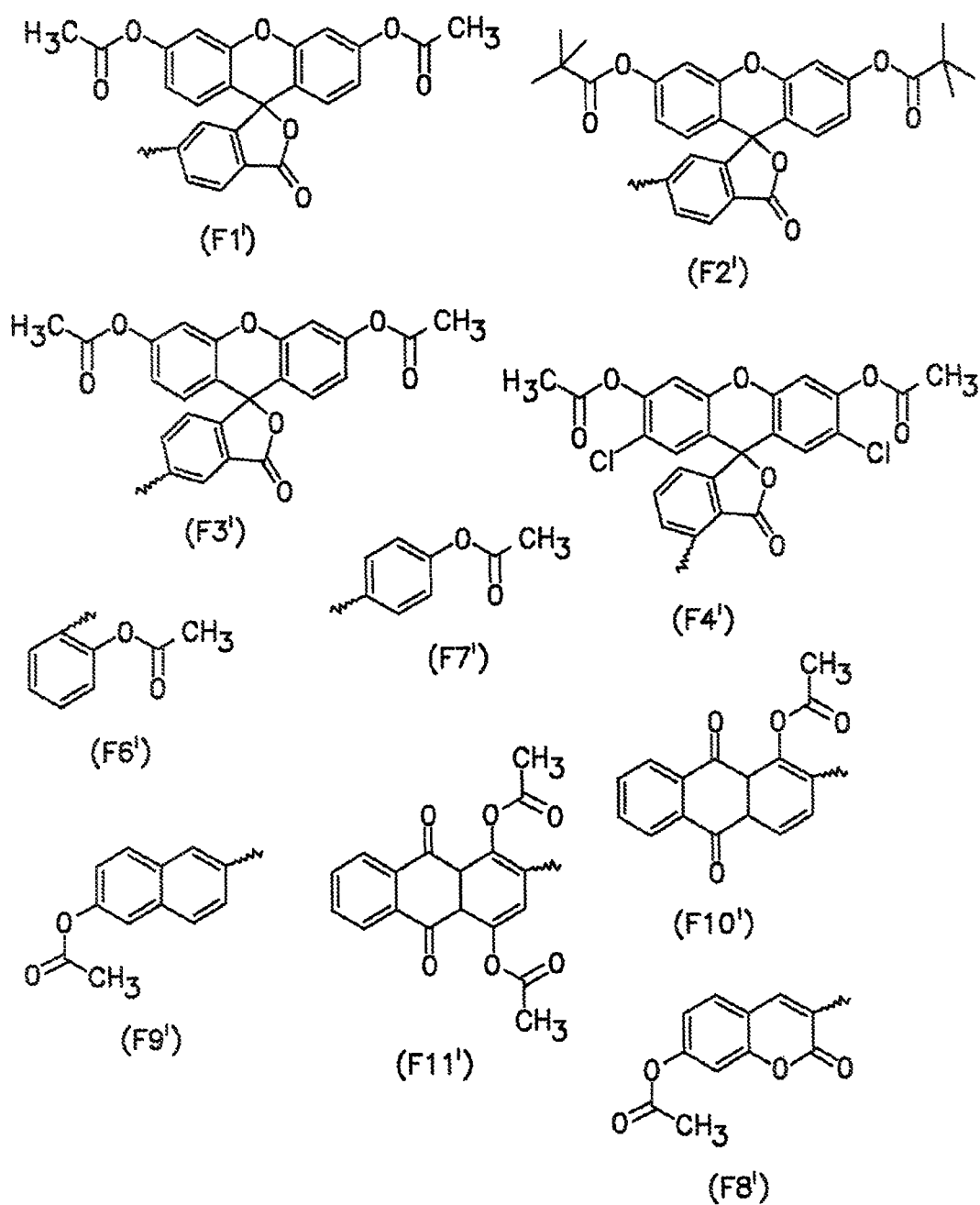
FIG. 1: The figure shows examples of aryl radicals of the formula (I).

The molecule to be transported can be any molecule. Preferably, the molecule to be transported has a molecular weight of ≧350 Dalton. One embodiment of the invention relates to conjugates where the molecule to be transported is a macromolecule, for example having a molecular weight ≧500 Dalton, preferably >1000 Dalton, particularly preferably >2000 Dalton or more.

The molecule to be transported can also be a low-molecular-weight compound, for example having a molecular weight <500 Dalton, preferably with a molecular weight of 350 to 500 Dalton. The low-molecular-weight compound can be a mononucleotide.

The molecule to be transported can belong to various chemical substance classes; for example, it can be a biopolymer, for example a polynucleotide, preferably an oligonucleotide, a polypeptide, preferably a peptide or protein, a peptide-nucleic acid (PNA) or a polyamide, which comprises the three aromatic rings imidazole, pyrrol and hydroxypyrrol (Kielkopf et al., *Science* 282:111-115 (1998)) or a polysaccharide, preferably an oligosaccharide, or a derivative of the compounds mentioned. The molecule to be transported can be a peptide mimetic.

Polynucleotides, oligonucleotides, and mononucleotides are either naturally occurring nucleic acids or known derivatives thereof. Derivatives are to be understood as meaning, inter alia, the salts derived from the conjugate or molecule to be transported, in particular physiologically acceptable salts thereof, and also, for example, modified or stabilized nucleic acids.

The molecule to be transported can be:
  (1) an inhibitor of transcription factors, e.g., NF-$_\kappa$B, c-fos or c-jun;
  (2) cell cycle proteins, e.g., cyclin D;
  (3) kinases, e.g., c-Src-, tyrosine or MAP kinases;
  (4) intracellular ion channels;
  (5) immunophilines, e.g., FK506 binding protein;
  (6) prolyl-4-hydroxylase;
  (7) topoisomerases;
  (8) viral proteases;
  (9) multiple drug resistance proteins; or
  (10) phosphatases, e.g., protein tyrosine phosphatase.

The molecule to be transported can be conjugated with one or more aryl radicals, for example two, three, four, five, six, seven, eight, nine, ten, fifteen, twenty, or more aryl radicals.

The aryl radical ("aryl radical" is in particular an aryl radical of the formula I and/or an aryl radical of the formula II) can be attached singly or more than once to the molecule to be transported, where the bonds can be localized at different positions of the aryl radical. If a plurality of aryl radicals is attached to the molecule to be transported, these can be identical or different.

The aryl radical contains an aryl group (referred to as "aryl" in the formulae I and II); the aryl group may comprise one or more rings, where at least one of the rings has aromatic character. The aryl group may also contain heterocyclic rings, which may or may not have aromatic character. The aryl group contains, for example, 1 to 8 or more rings (also "ring system"), preferably 1, 2, 3, 4, 5, 6, 7 or 8 rings. The individual rings have a size of 3 to 7 ring atoms, preferably 5 to 6 ring atoms. Examples of ring systems are phenyl rings, pyridinyl rings, pyrimidinyl rings, pyrrolyl rings, furanyl rings, thiophenyl rings, 5-membered lactones, 6-membered lactones, spirolactones, benzoquinones, cyclohexadienyl rings and cyclohexenyl rings. These ring systems; the aryl group or individual rings of the aryl group can be mono- or polysubstituted. Preferably at least one of the rings of the aryl group carries an acyl radical.

The aryl group can, for example, have one of the formulae F1', F2', F3', F4', F6', F7', F8', F9', F10', F11'. These formulae are shown in FIG. 1.

The aryl radical can be attached directly to the molecule to be transported, or via a chemical group. The invention provides a conjugate wherein the chemical group together with the aryl radical has the formula II

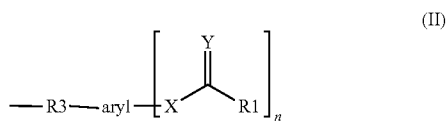

(II)

wherein aryl, X, Y and $R^1$ are as defined above and $R^3$ is the chemical group, $R^3$ being, for example, a —C(═O) group or an —NH—C(═S) group.

Figure 2A:
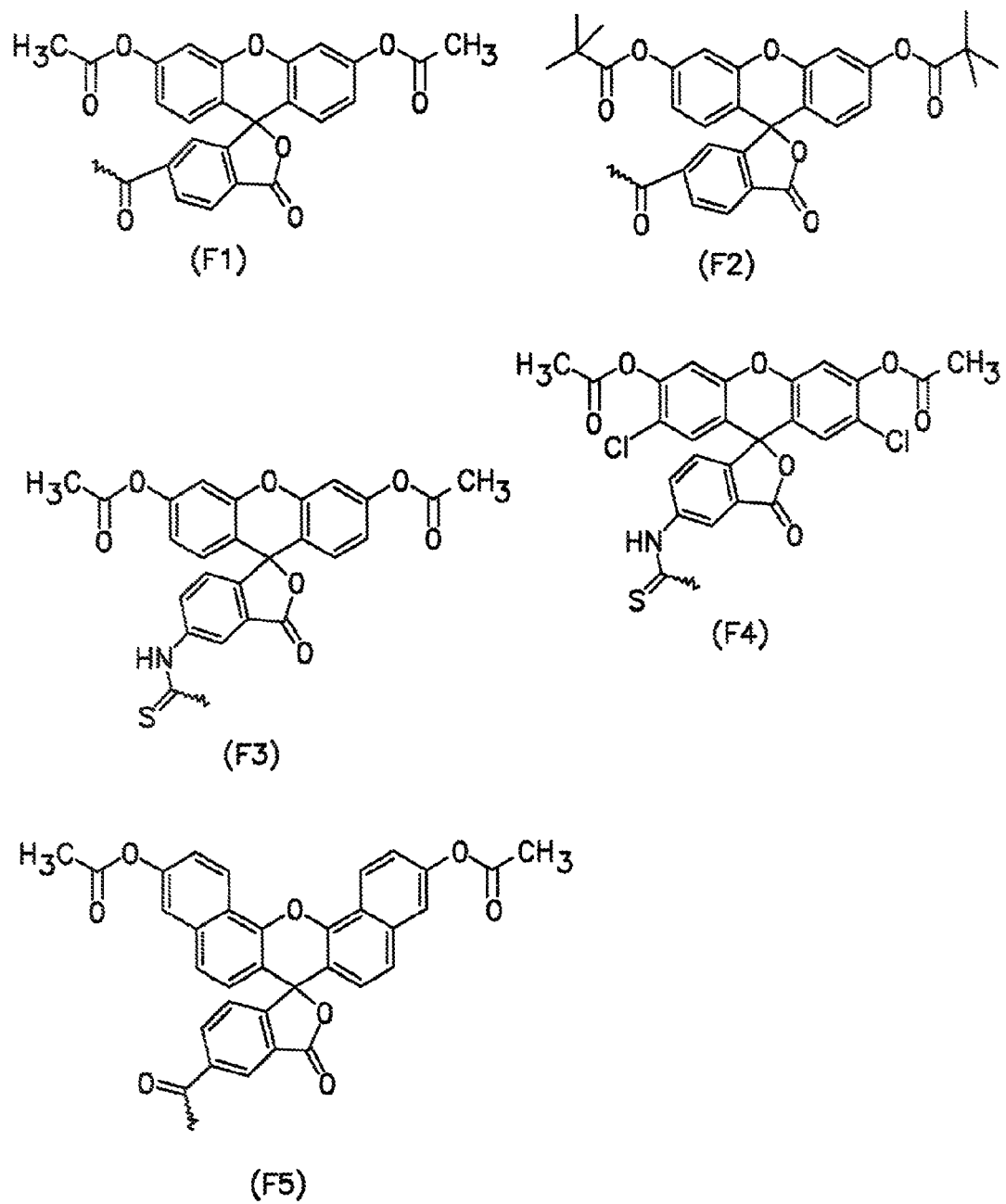
FIGS. 2a and 2b: The figures show examples of aryl radicals of the formula (II).
Figure 2B:
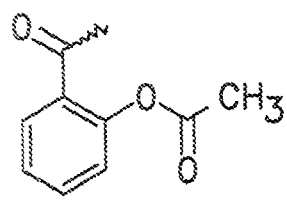
Figure 2B:
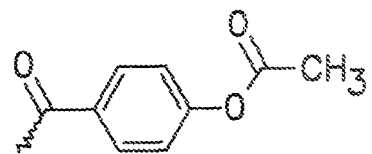
Figure 2B:
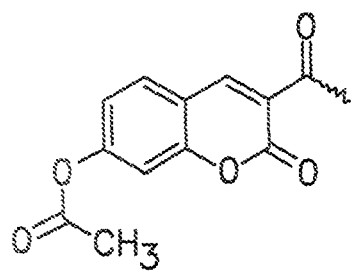
Figure 2B:
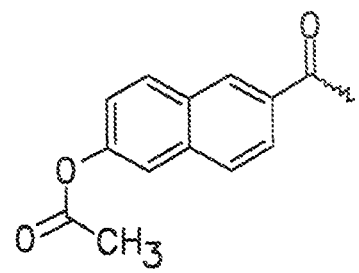
Figure 2B:
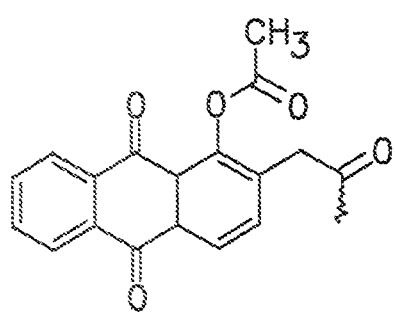
Figure 2B:
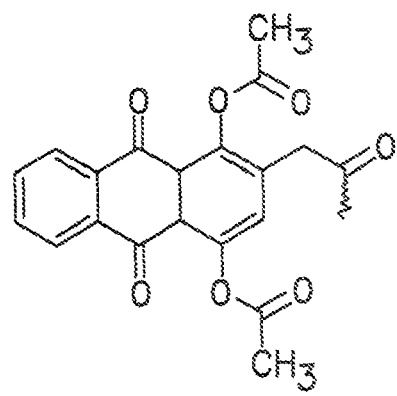

Examples of aryl radicals of the formula II are the aryl radicals of the formulae F1, F2, F3, F4, F5, F6, F7, F8, F9, F10 and F11; these formulae are shown in FIG. 2a and FIG. 2b.

In a particular embodiment, the molecule to be transported is an oligonucleotide. An oligonucleotide can, for example, be constructed entirely of the nucleotides adenosine phosphate, guanosine phosphate, inosine phosphate, cytidine phosphate, uridine phosphate, and thymidine phosphate. In other embodiments of the invention, an oligonucleotide may, if appropriate, contain one or more modifications, for example, chemical modifications. An oligonucleotide may have a plurality of identical and/or different modifications.

Examples of chemical modifications are known to the person skilled in the art and described, for example, in E. Uhlmann and A. Peyman, Chemical Reviews 90 (1990) 543 and "Protocols for Oligonucleotides and Analogs" *Synthesis and*

*Properties & Synthesis and Analytical Techniques*, S. Agrawal, Ed., Humana Press, Totowa, USA 1993; and J. Hunziker and C. Leumann "Nucleic Acid Analogs: Synthesis and Properties" in *Modern Synthetic Methods* (Ed. Beat Ernst and C. Leumann), Verlag Helvetica Chimica Acta, Basel, pp. 331-417.

The chemical modification of an oligonucleotide may comprise, for example:

a) the complete or partial replacement of the phosphodiester bridges, for example by phosphorothioate, phosphorodithioate, $NR^1R^{1'}$-phosphoramidate, boranophosphate, phosphate $(C_1-C_{21})$—O-alkyl ester, phosphate $[(C_6-C_{12})$-aryl-$(C_1-C_{21})$—O-alkyl]ester, $(C_1-C_8)$-alkylphosphonate and/or $(C_6-C_{12})$-arylphosphonate bridges, where $R^1$ and $R^{1'}$ independently of one another are hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl and/or methoxyethyl, particularly preferably hydrogen, $(C_1-C_4)$-alkyl and/or methoxyethyl, or $R^1$ and $R^{1'}$ form, together with the nitrogen atom carrying them, a 5- to 6-membered heterocyclic ring which can additionally contain a further hetero atom from the group consisting of O, S and N;

b) the complete or partial replacement of the 3'- and/or 5'-phosphodiester bridges by "dephospho" bridges (described, for example, in Uhlmann, E. and Peyman, A. in *Methods in Molecular Biology, Vol.* 20, "Protocols for Oligonucleotides and Analogs", S. Agrawal, Ed., Humana Press, Totowa (1993), Chapter 16, 355ff.), for example by formacetal, 3'-thioformacetal, methylhydroxylamine, oxime, methylenedimethylhydrazo, dimethylenesulfone and/or silyl groups;

c) the complete or partial replacement of the sugar phosphate backbone, for example by "morpholino" oligomers (described, for example, in E. P. Stirchak et al., *Nucleic Acids Res.* 17:6129 (1989) and in J. Summerton and D. Weller, *Antisense and Nucleic Acid Drug Dev.* 7:187-195 (1997)) and/or by polyamide nucleic acids ("PNAs") (described, for example, in P. E. Nielsen et al., *Bioconj. Chem.* 5:3 (1994)) and/or phosphonic acid monoester nucleic acids ("PHONAs") (described, for example, in Peyman et al., *Angew. Chem. Int. Ed. Engl.* 35:2632-2638 (1996));

d) the complete and/or partial replacement of the β-D-2'-deoxyribose units, for example by α-D-2'-deoxyribose, L-2'-deoxyribose, 2'-F-2'-deoxyribose, 2'-O—$(C_1-C_6)$-alkyl-ribose, 2'-O—$(C_2-C_6)$-alkenyl-ribose, 2'-[O—$(C_1-C_6)$-alkyl-O—$(C_1-C_6)$-alkyl]-ribose, 2'—$NH_2$-2'-deoxyribose, β-D-xylofuranose, α-arabinofuranose, 2,4-dideoxy-β-D-erythrohexopyranose, conformationally restricted sugar analogs such as LNA (locked nucleic acids; Singh et al., *Chem. Commun.* 4:455 (1998); Singh et al. *Chem. Commun.* 12:1247 (1998)) and carbocyclic (described, for example, in Froehler, *J. Am. Chem. Soc.* 114:8320 (1992)) and/or open-chain sugar analogs (described, for example, in Vandendriessche et al., *Tetrahedron* 49 (1993) 7223) and/or bicyclosugar analogs (described, for example, in M. Tarkov et al., *Helv. Chim. Acta* 76:481 (1993));

e) modification and/or complete or partial replacement of the natural nucleoside bases, for example, by 5-(hydroxymethyl) uracil, 5-aminouracil, pseudouracil, pseudoisocytosine, dihydrouracil, 5-$(C_1-C_6)$-alkyl-uracil, 5-$(C_2-C_6)$-alkenyl-uracil, 5-$(C_2-C_6)$-alkynyl-uracil, 5-$(C_1-C_6)$-alkyl-cytosine, 5-$(C_2-C_6)$-alkenyl-cytosine, 5-$(C_2-C_6)$-alkynyl-cytosine, 5-fluorouracil, 5-fluorocytosine, 5-chlorouracil, 5-chlorocytosine, 5-bromouracil, 5-bromocytosine, or 7-deaza-7-substituted purines.

The chemical modification of an oligonucleotide, furthermore, embraces the attachment of an oligonucleotide to one or more further molecules having a favorable effect on particular properties of the oligonucleotide. These effects include, for example, stability to nucleases, affinity to the target sequence and pharmacokinetics, and, for example, binding to and/or crosslinking the target sequence during hybridization of the modified oligonucleotide with the target sequence. Examples of such further molecules are polylysine, intercalating agents, such as pyrene, acridine, phenazine or phenanthridine, fluorescent compounds, such as fluorescein, crosslinking agents, such as psoralen or azidoproflavine, lipophilic molecules, such as $(C_{12}-C_{20})$-alkyl groups, preferably $(C_{12}-C_{20})$-alkyl groups, lipids, such as 1,2-dihexadecyl-rac-glycerol, steroids, such as cholesterol or testosterone, vitamins, such as vitamin E, poly- or oligoethylene glycol, $(C_{12}-C_{18})$-alkyl phosphate diesters, preferably $(C_{14}-C_{18})$-alkyl phosphate diesters and, —O—$CH_2$—CH(OH)—O—$(C_{12}-C_{18})$-alkyl groups, preferably —O—$CH_2$—CH(OH)—O—$(C_{12}-C_{16})$-alkyl groups. These further molecules may be conjugated at the 5'- and/or the 3'-end and/or within the sequence, for example to a nucleobase. The processes for preparing such modified oligonucleotides are known to the person skilled in the art and described, for example, in Uhlmann, E. & Peyman, A., *Chem. Rev.* 90 (1990) 543 and/or M. Manoharan in *Antisense Research and Applications*, Crooke and Lebleu, Eds., CRC Press, Boca Raton, 1993, Chapter 17, p. 303ff. and/or EP-A 0 552 766.

In further specific embodiments of the invention, the oligonucleotide may have 3'-3' and/or 5'-5' inversions at the 3'- and/or the 5'-end. This type of chemical modification is known to the person skilled in the art and described, for example, in M. Koga et al., *J. Org. Chem.* 56:3757 (1991).

Figure 3:
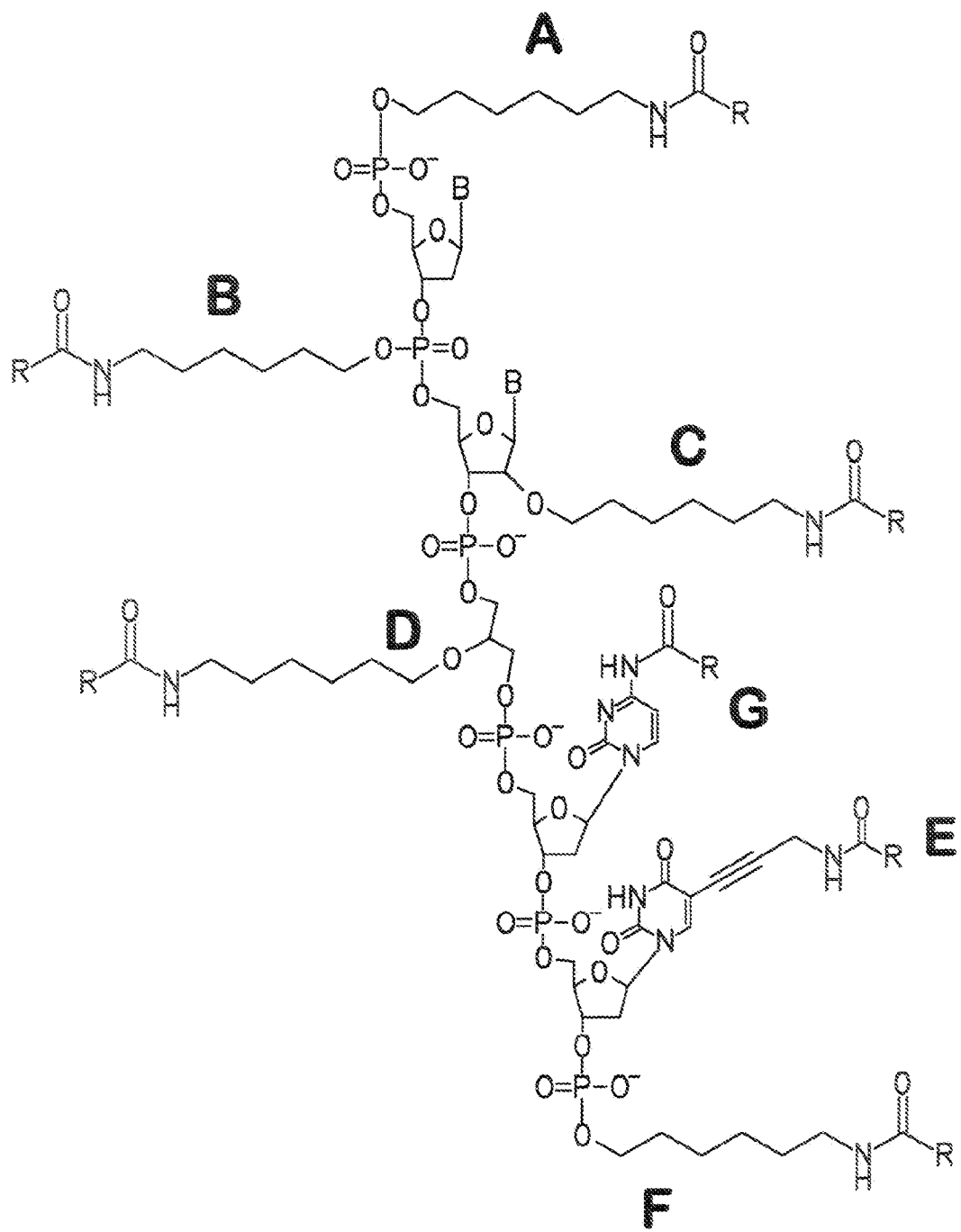
FIG. 3.

In a conjugate, which consists of one or more oligonucleotides and one or more aryl radicals, preferably of the formula I or II, the conjugation of aryl radicals to an oligonucleotide can take place, for example, at the 5'-end (A), at the 3'-end (F), at the heterocyclcic base (E and G), at the sugar (C) or at the internucleoside bridge (B) of the oligonucleotide. However, conjugation can also take place, for example, via non-nucleotidic building blocks, for example in the case (D). These examples are shown in FIG. 3.

The modifications mentioned can, of course, also be applied correspondingly to relatively long polynucleotides and, if suitable, to mono- or dinucleotides or -nucleosides.

The oligonucleotides have, for example, a length of 8 to 50 nucleotides, preferably 10-20 nucleotides. However, oligonucleotides having longer oligo- or polynucleotides, for example of a length of from 50 to 10,000 nucleotides, preferably from 100 to 1000 nucleotides, which may, if appropriate, also be present as a double strand, are also suitable.

The oligonucleotides may have any sequence. The sequence of the oligonucleotide is selected or designed depending on the selected target, i.e., if the target is a nucleic acid, depending on its sequence, or, if the target is a protein, depending on the nucleic acid sequence which encodes this target protein. If, for example, the target is a virus, e.g., CMV, HIV, HSV-1, HSV-2, influenza, VSV, hepatitis B, or papilloma virus, the oligonucleotide may, for example, have one of the following sequences:

a) against CMV

SEQ ID NO. 12
5'-G C G T T T G C T C T T C T T C T T G C G b) against HIV, for example 5'-A C A C C C A A T T C T G A A A A T G G-3'    SEQ ID NO. 13
or
5'-A G G T C C C T G T T C G G G C G C C A-3'    SEQ ID NO. 14 c) against HSV-1, for example

5'-G C G G G G C T C C A T G G G G G T C G-3'    SEQ ID NO. 15

The target can, for example, be a protein, which is involved in the formation of cancer or responsible for cancer growths. Examples of such targets are:

1) nuclear oncoproteins, such as, for example, c-myc, N-myc, c-myb, c-fos, c-fos/jun, PCNA, p120;
2) cytoplasmic/membrane-associated oncoproteins, such as, for example, EJ-ras, c-Ha-ras, N-ras, rrg, bcl-2, cdc-2, c-raf-1, c-mos, c-src, c-abl, c-ets;
3) cellular receptors, such as, for example, EGF receptor, Her-2, c-erbA, VEGF receptor (KDR-1), retinoid receptors, the regulatory subunit of protein kinase, c-fms, Tie-2, c-raf-1 kinase, PKC-alpha, protein kinase A (R1 alpha);
4) cytokines, growth factors, extracellular matrixes, such as, for example, CSF-1, IL-6, IL-1a, IL-1b, IL-2, IL-4, IL-6, IL-8, bFGF, VEGF, myeloblastin, fibronectin.

Oligonucleotides which are directed against such targets can, for example, have the following base sequence:

a) against c-Ha-ras, for example

5'-C A G C T G C A A C C C A G C-3'    SEQ ID NO. 16
or
5'-T A T T C C G T C A T-3'    SEQ ID NO. 17
or
5'-T T C C G T C A T C G C T C C T C A G G G G-3'    SEQ ID NO. 18 b) bFGF, for example

5'-G G C T G C C A T G G T C C C-3'    SEQ ID NO. 19 c) c-myc, for example

5'-G G C T G C T G G A G C G G G G C A C A C-3'    SEQ ID NO. 20
5'-A A C G T T G A G G G G C A T-3'    SEQ ID NO. 21 d) c-myb, for example

5'-G T G C C G G G G T C T T C G G G C-3'    SEQ ID NO. 22 e) c-fos, for example

5'-C G A G A A C A T C A T C G T G G-3'    SEQ ID NO. 23
5'-G G A G A A C A T C A T G G T C G A A A G-3'    SEQ ID NO. 24
5'-C C C G A G A A C A T C A T G G T C G A A G-3'    SEQ ID NO. 25
5'-G G G G A A A G C C C G G C A A G G G G-3'    SEQ ID NO. 26 f) p120, for example

5'-C A C C C G C C T T G G C C T C C C A C-3'    SEQ ID NO. 27 g) EGF receptor, for example

5'-G G G A C T C C G G C G C A G C G C-3'    SEQ ID NO. 28
5'-G G C A A A C T T T C T T T T C C T C C-3'    SEQ ID NO. 29 h) p53 tumor suppressor, for example

5'-G G G A A G G A G G A G G A T G A G G-3'    SEQ ID NO. 30
5'-G G C A G T C A T C C A G C T T C G G A G-3'    SEQ ID NO. 31 i) bcl-2

5'-TCTCCCAGCGTGCGCCAT    SEQ ID NO. 32 k) VEGF

5'-G C G C T G A T A G A C A T C C A T G    SEQ ID NO. 33
3'- CCAGCCCGGAGG -5', 5'-GGAGGCCCGACC-3'    SEQ ID NO. 34
3'- CGGAGGCTTTGG -5', 5'-GGTTTCGGAGGC-3';    SEQ ID NO. 35
3'- GATGGAGGTGGT -5', 5'-TGGTGGAGGTAG-3'    SEQ ID NO. 36
3'- GGAGGTGGTACG -5', 5'-GCATGGTGGAGG-3'    SEQ ID NO. 37
3'- GGTGGTACGGTT -5', 5'-TTGGCATGGTGG-3'    SEQ ID NO. 38
3'- CACCAGGGTCCG -5', 5'-GCCTGGGACCAC-3'    SEQ ID NO. 39
3'- CCAGGGTCCGAC -5', 5'-CAGCCTGGGACC-3'    SEQ ID NO. 40
3'- AGGGTCCGACGT -5', 5'-TGCAGCCTGGGA-3'    SEQ ID NO. 41
3'- GGGTCCGACGTG -5', 5'-GTGCAGCCTGGG-3'    SEQ ID NO. 42
3'- GGTCCGACGTGG -5', 5'-GGTGCAGCCTGG-3'    SEQ ID NO. 43
3'- CCGACGTGGGTA -5', 5'-ATGGGTGCAGCC-3'    SEQ ID NO. 44

-continued

```
                                    SEQ ID NO. 45
3'- GTAGAAGTTCGG -5',  5'-GGCTTGAAGATG-3'

SEQ ID NO. 46
3'- ACGCCCCCGACG -5',  5'-GCAGCCCCCGCA-3'
or
                                    SEQ ID NO. 47
3'- CCCCCGACGACG -5',  5'-GCAGCAGCCCCC-3'
``` l) c-raf kinase

```
5'- TCCCGCCTGTGACATGCATT      SEQ ID NO. 48
``` m) PKC-alpha

```
5'-GTTCTCGCTGGTGAGTTTCA       SEQ ID NO. 49
``` n) protein kinase A

```
5'-GCGTGCCTCCTCACTGGC         SEQ ID NO. 50
```

If the target is an integrin or a cell-cell adhesion receptor, such as, for example, VLA-4, VLA-2, ICAM, VCAM or ELAM, the oligonucleotide can, for example, have one of the following sequences:

a) VLA-4, for example

```
                                    SEQ ID NO. 51
5'-G C A G T A A G C A T C C A T A T C-3'
or
``` b) ICAM-1, for example

```
                                    SEQ ID NO. 52
5'-G C C C A A G C T G G C A T C C G T C A

SEQ ID NO. 53
5'-C C C C A C C A C T T C C C C T C T C-3'

SEQ ID NO. 54
5'-C T C C C C C A C C A C T T C C C C T C-3'

SEQ ID NO. 55
5'-G C T G G G A G C C A T A G C G A G G-3'
``` c) ELAM-1, for example

```
                                    SEQ ID NO. 56
5'-A C T G C T G C C T C T T G T C T C A G G-3'

SEQ ID NO. 57
5'-C A A T C A A T G A C T T C A A G A G T T C-3'
``` d) integrin alpha(V)

```
5'-GCGGCGGAAAAGCCATCG         SEQ ID NO. 58
```

If the target is a protein which is responsible for proliferation or migration or involved in these/this process(es), such as, for example;
1) nuclear transactivator proteins and cyclines, such as, for example, c-myc, c-myb, c-fos, c-fos/jun, cyclines and cdc2 kinase;
2) mitogens or growth factors, such as, for example, PDGF, bFGF, VEGF, EGF, HB-EGF and TGF-1;
3) cellular receptors, such as, for example, bFGF receptor, EGF receptor and PDGF receptor; the oligonucleotide can, for example, have one of the following base sequences:

a) c-myb

```
                                    SEQ ID NO. 59
5'-G T G T C G G G G T C T C C G G G C-3'
``` b) c-myc

```
5'-C A C G T T G A G G G G C A T-3'   SEQ ID NO. 60
``` c) cdc2 kinase

```
                                    SEQ ID NO. 61
5'-G T C T T C C A T A G T T A C T C A-3'
``` d) PCNA (proliferating cell nuclear antigen of rat)

```
                                    SEQ ID NO. 62
5'-G A T C A G G C G T G C C T C A A A-3'.
```

If the target is, for example, an adenosine A1 receptor, adenosine A3 receptor, bradykinin receptor or IL-13, the base sequence

```
5'-GATGGAGGGCGGCATGGCGGG      SEQ ID NO. 63
``` is, for example, possible.

The following oligonucleotides (5'—>3') were prepared:

```
ON1:
5'-d(G*C G A C*G C*C A T*G A C*G*G)    SEQ ID NO. 1

ON2:
5'-d(C*G A C*G C*C A T*G*A*C)          SEQ ID NO. 2

ON3:
5'-d(A*T*G A C*G G A A*T*T*C)          SEQ ID NO. 3

ON4:
5'-d(T A T T C C G T C A T)            SEQ ID NO. 4

ON5:
5'-(dA)20                              SEQ ID NO. 5

ON6:
5'-(dA)50                              SEQ ID NO. 6

ON7:
5'-(dA)80                              SEQ ID NO. 7

ON8:
5'-T*T*C C*A T*G G*T G*G*C             SEQ ID NO. 8

ON9:
5'-T*T*C A*C T*G T*G G*G*C             SEQ ID NO. 9

ON10:
5'-T*G*G C*G C*C G*G G*C*C             SEQ ID NO. 10

ON11:
5'-T*G*C C*G G*C C*G G*G*C             SEQ ID NO. 11
``` where * indicates the positions at which a phosphodiester bridge has been replaced by a phosphorothioate internucleoside bridge.

These sequences were converted into the following conjugates (CO):

| | |
|---|---|
| CO_1: | F3-Li1-ON1 |
| CO_2: | F0-Li1-ON1 |

-continued

| CO_3: | F3-Li1-ON2 |
| CO_4: | F0-Li1-ON2 |
| CO_5: | F3-Li1-ON3 |
| CO_6: | F9-Li1-ON3 |
| CO_7: | F2-Li-1ON3 |
| CO_8: | F0-Li1-ON3 |
| CO_9: | F3-Li1-ON3-rhodamine |
| CO_10: | F9-Li1-ON3-rhodamine |
| CO_11: | F6-Li1-ON3-rhodamine |
| CO_12: | F0-Li1-ON3-rhodamine |
| CO_13: | F3-Li1-ON4 |
| CO_14: | F3-Li1-ON5 |
| CO_15: | F3-Li1-ON6 |
| CO_16: | F3-Li1-ON7 |
| CO_17: | F3-Li1-ON8 |
| CO_18: | F3-Li1-ON9 |
| CO_19: | F3-Li1-ON10 |
| CO_20: | F3-Li1-ON11 |
| CO_21: | F7-Li1-ON3 | where
"F1 to F11" are aryl radicals of the formulae F1 to F11 (e.g., FIG. 2); "L1i" is a 6-aminohexyl phosphate radical, which is attached to the 5'-end of the oligonucleotide (e.g., Figure see enclosure 4);
"ON1 to ON11" are the described oligonucleotides of the sequences SEQ ID NO.1 to SEQ ID NO.11; and "rhodamine" is a rhodamine label at the 3'-end of the oligonucleotide, which is detectable in addition to fluorescein.

The invention also provides processes for preparing the conjugates according to the invention. The invention relates to processes for preparing a conjugate which comprises a molecule to be transported and at least one aryl radical, preferably of the formula I or II, where
a) a molecule to be transported which contains a reactive function at the position to which the aryl radical is to be attached is prepared;
b) an aryl radical is prepared; and
c) the molecule to be transported is reacted with the aryl radical to give the conjugate.

The reactive function is preferably an amino group, mercapto group, chloroacetyl group, isocyanate group, isothiocyanate group, carboxylic acid group, N-hydroxysuccinimide group or a carbonyl chloride group. The reaction of the molecule to be transported with the aryl radical is carried out at a pH≦7.5; preferably at a pH≦7.3, particularly preferably at a pH of 7.0 or a lower pH, for example a pH<7, preferably a pH≦6.5. In these coupling reactions, all other reactive groups have to be protected prior to the reaction using protective groups known to the person skilled in the art. In a particular embodiment of the processes, the molecule to be transported is a polynucleotide, oligonucleotide, or mononucleotide.

The preparation processes comprise, in a first step, the preparation of the molecule to be transported. In this context, the invention also relates to processes for preparing oligonucleotides. The oligonucleotides can be prepared with the aid of various known chemical processes, for example as described in Eckstein, F. (1991) "Oligonucleotides and Analogues, A Practical Approach", IRL Press, Oxford. The oligonucleotides can also be prepared by processes, which, if appropriate, comprise one or more enzymatic steps. The preparation of oligonucleotide conjugates is, in principle, described in the literature (J. Goodchild, Bioconjugate Chem. 1 (1990) 165; S. Beaucage and R. Iyer, Tetrahedron 49 (1993) 1925; S. Agrawal Methods in Molecular Biology Vol. 26 "Protocols for oligonucleotide conjugates" (1994) Humana Press).

Figure 5:
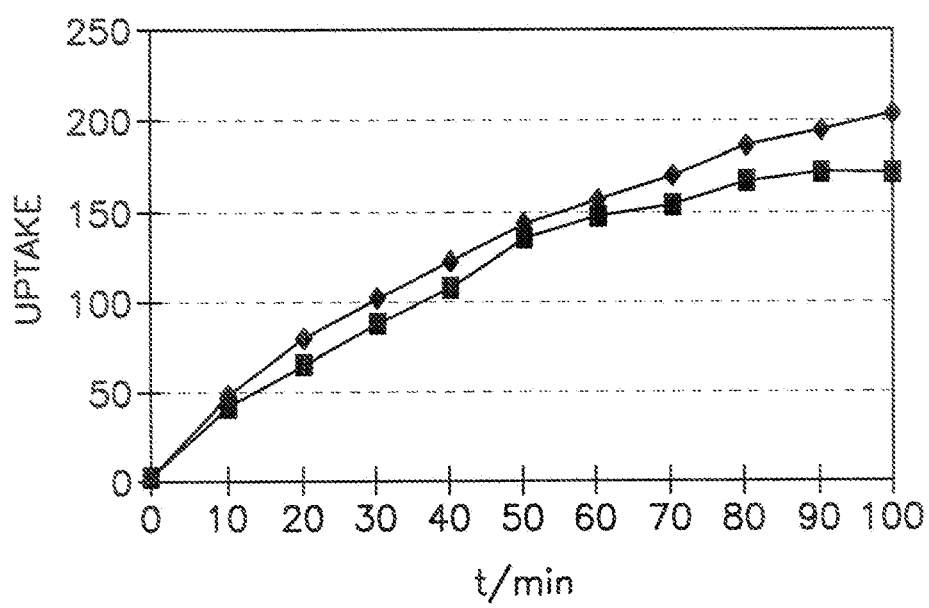
FIG. 5.
Figure 6:
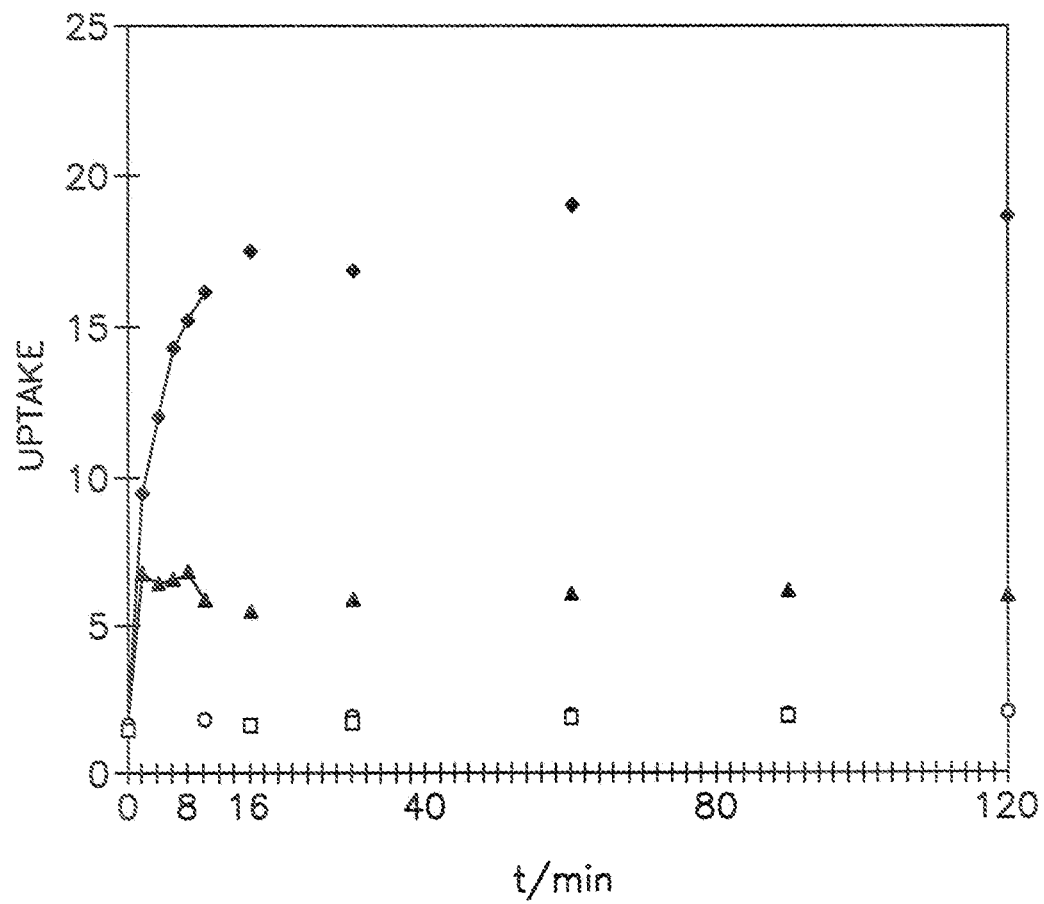
FIG. 6: Diagram of the determination of the uptake of CO_1 (FDA conjugate; ♦) and CO_2 (FITC oligomer; ▲) into the cell by FACS measurement. The initial concentration of extracellular oligonucleotide conjugate was 1 µM; ○ and □ a are controls.
Figure 7:
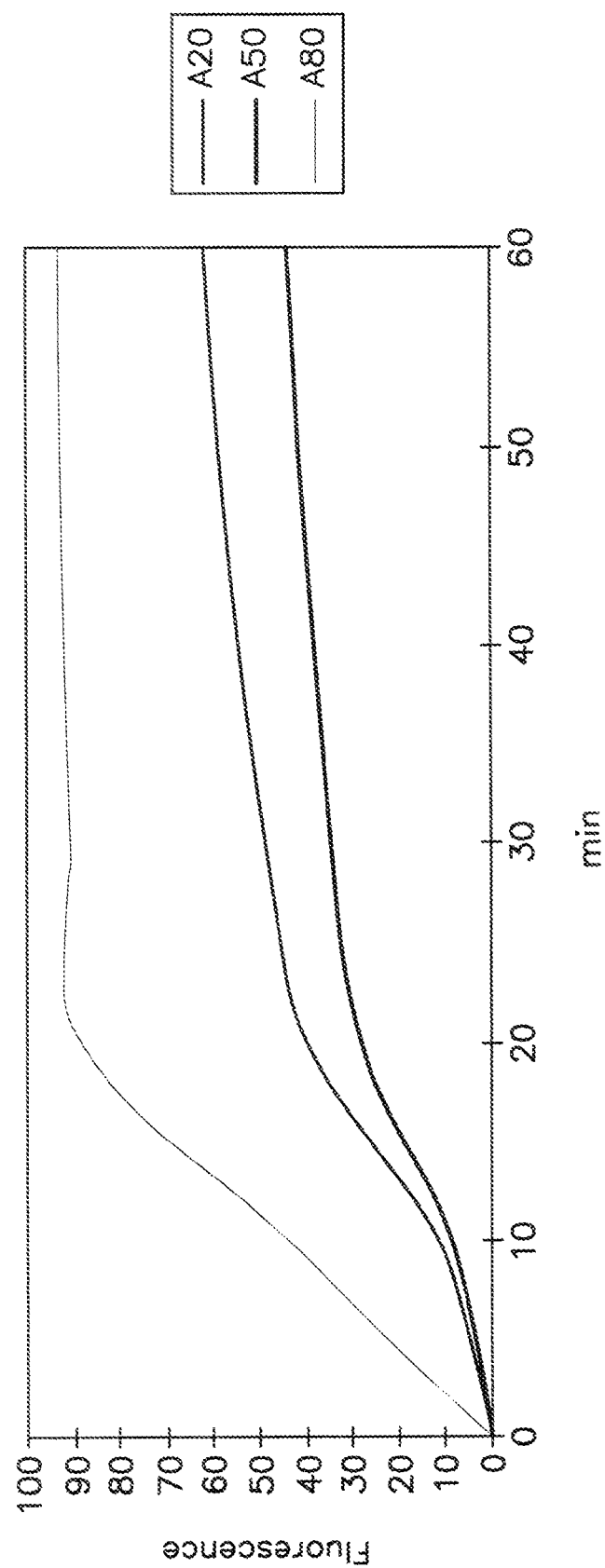
FIG. 7: The transfection of FDA-conjugated polyA-nucleotides in REH cells as a function of the length

However, when synthesizing the oligonucleotide conjugates according to formula I, attention has to be paid to the fact that they may decompose in alkaline medium. It is therefore not possible, for example, to synthesize FDA-labeled oligonucleotides in an oligonucleotide synthesizer using the customary methods, because the ester groups of the FDA group would hydrolyze during the treatment with ammonia required for cleaving the oligonucleotide from the support and for cleaving the amino protective groups of the heterocyclic bases. Thus, the oligonucleotide is initially prepared as a precursor in deprotected form and fused with the group of formula I in the last step (FIG. 5). The oligonucleotide precursor has a reactive or activatable function, which is subsequently derivatized by methods known to the person skilled in the art with a reagent, which contains the group of the formula I according to the invention. Suitable reactive or activatable functions are, for example, amino, mercapto, chloroacetyl, iso(thio)cyanate and carboxylic acid functions. It is particularly easy to introduce so-called amino linkers with the aid of commercially available reagents into oligonucleotides. The amino-linker oligonucleotides are then reacted, for example, with reactive reagents, which contain a group of the formula I. Such reactive reagents are, for example, the corresponding isothiocyanates. The group of the formula I is in this case attached via a thiourea function (Enclosure 4). Other reactive reagents are, for example, the carbonyl chlorides. Mild reactive reagents are, for example, the N-hydroxysuccinimides of the corresponding carboxylic acids. Activatable reagents are, for example, the corresponding carboxylic acids, which can be coupled with peptide coupling reagents such as HBTU, TBTU or TOTU. In this case, the group of the formula I is attached via an amide function. In principle, the groups of the formula I according to the invention can be introduced into any positions of the oligonucleotide. Preference is given to the positions shown in FIG. 3.

The modified oligonucleotides were synthesized by constructing the oligonucleotide chain by standard methods, such as the solid-phase synthesis by the phosphoramidite method, and derivatization of the 5'-end with commercially available 5'-amino-modifier $C_6$ (for example from Eurogentec, Seraing, Belgium).

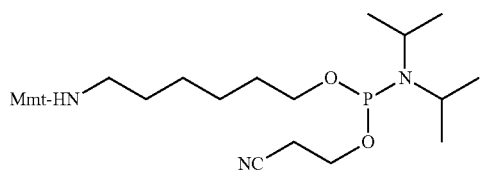

5'-Amino-modifier C6 (Mmt=4-Monomethoxytrityl)

Figure 4:
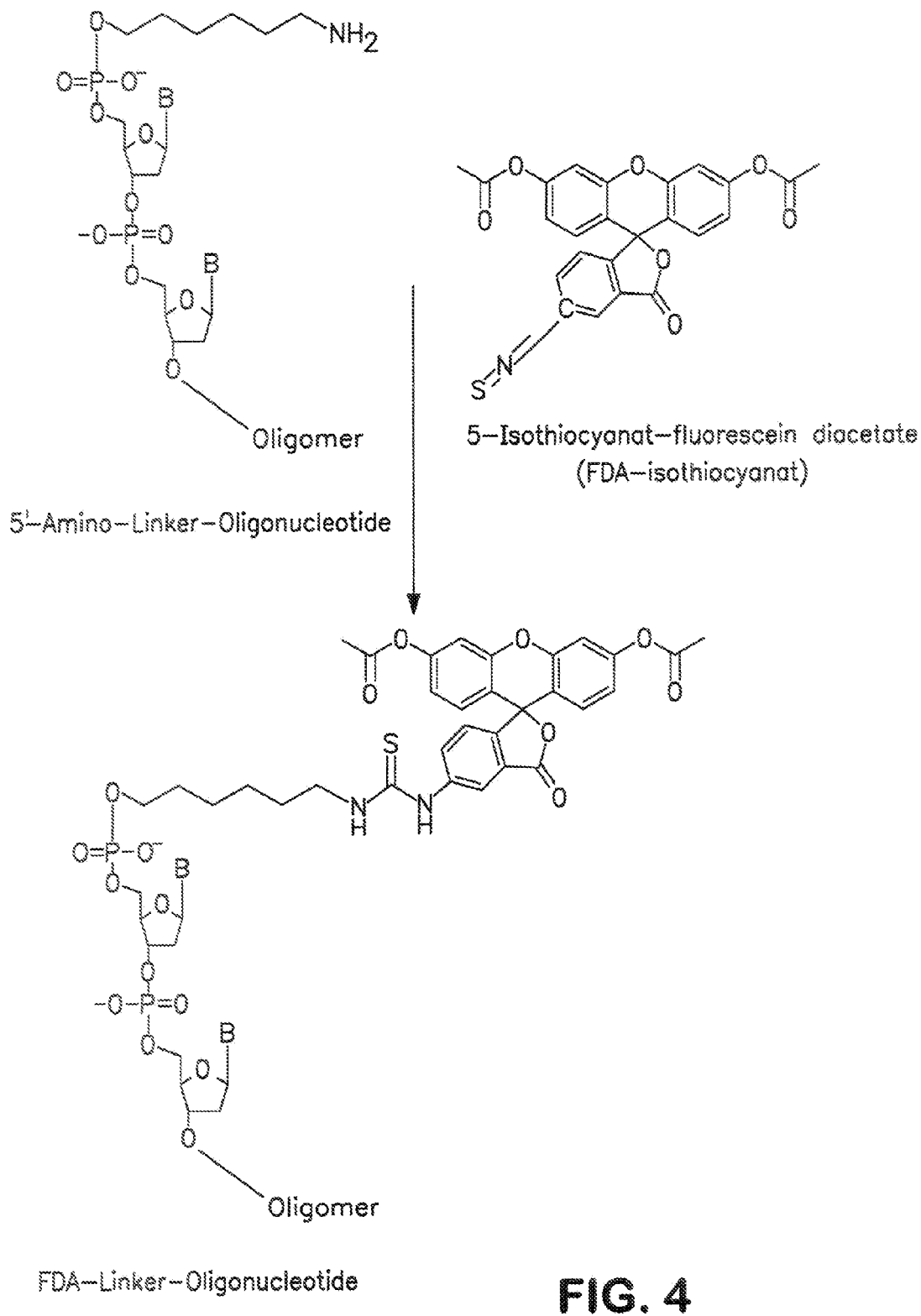
FIG. 4.

After cleavage of the oligonucleotide derivative from the support and deprotection of all base-labile protective groups by treatment with ammonia, the monomethoxytrityl group is removed by treatment with 80% acetic acid at ambient temperature. This gives a 5'-aminohexyl-phosphate-modified oligonucleotide. The amino function of this oligonucleotide derivative is then reacted with FDA-isothiocyanate in 0.2 M triethylammonium bicarbonate buffer (TBK buffer) pH 7/DMF. After only two to three hours, the amino-linker oligonucleotide had been converted completely into the desired FDA derivative (FIG. 4). Reactions with fluorescein isothiocyanate are usually carried out at pH 8. However, at this pH, the diacetate of the FDA group is hydrolyzed. It is, of course, also possible to use other amino-linker reagents, such as, for example, the 5'-amino-modifier C3, 5'-amino-modifier C12, 5'-amino-modifier 5 or 5'-thiol-modifier C6 (all from Eurogentec).

By using 3'-amino-modifier solid phases, such as, for example, 3'-amino-modifier C3 CPG (from Eurogentec), it is possible to prepare oligonucleotide derivatives having a 3'-aminoalkyl group, which are subsequently reacted with FDA-isothiocyanate. This gives an oligonucleotide derivative which contains the group of the formula I according to the invention attached at the 3'-end.

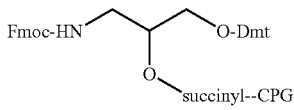

3'-Amino-Modifier C3 CPG (Fmoc=Fluorenylmethoxycarbonyl)

To introduce the conjugate at the heterocyclic base of the nucleoside, it is possible to use in the synthesis in place of a normal phosphoramidite building block a corresponding amino-modifier C6 dT (from Eurogentec) derived from thymidine. At the end of the oligonucleotide synthesis, the trifluoroacetyl protective group is removed by treatment with ammonia, and the free amino function is reacted in solution with FDA-isothiocyanate.

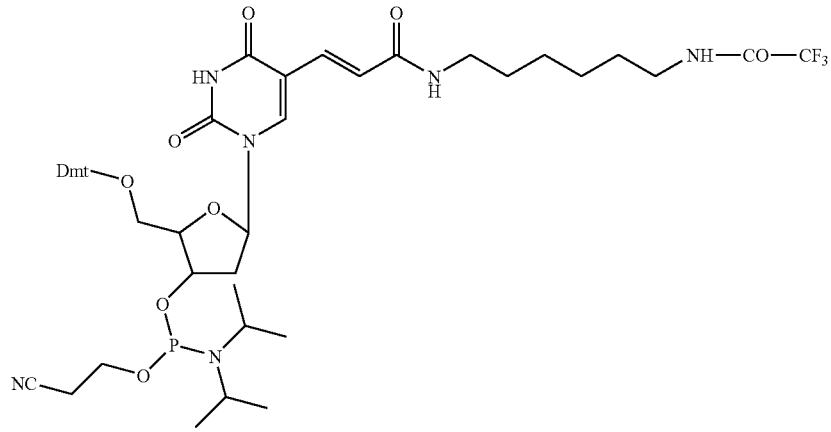

Amino-Modifier C6 dT

In a similar manner, it is possible to introduce the groups of the formula I according to the invention in any positions of the oligonucleotides. It can easily be seen that even a multiple introduction of identical or different groups is possible.

In processes for the preparation of conjugates in which the molecule to be transported is a peptide nucleic acid (PNAs), it is possible, for example, to react the primary amino function of the amino ethyl group with FDA-isothiocyanate. In processes for preparing conjugates in which the molecule to be transported is a polypeptide, it is possible to use, for example, the amino terminus of the polypeptide or the amino functions of lysine side-chains for a reaction with FDA-isothiocyanate.

The present invention also provides the uses of the conjugates, in particular uses based on the above-described advantageous properties of the conjugates. A particular embodiment of the invention relates to the use of the conjugates for transporting a molecule across a biological membrane. The invention also relates to the use of aryl radicals, preferably of the formula I or II, for transporting a molecule to which this aryl radical is attached across a biological membrane. The biological membrane is preferably a component of a cell, a vesicle or an organelle.

The present invention also provides methods for transporting a molecule across a membrane, where
a) a conjugate is prepared in which the molecule to be transported is attached to at least one aryl radical of the formula I or II, and
b) the conjugate is incubated with the membrane.

The present invention provides in particular methods for transporting a molecule into a cell, where
a) a conjugate is prepared in which the molecule to be transported is attached to at least one aryl radical of the formula I or II, and
b) the conjugate is incubated with the cell, whereupon
c) the conjugate is transported into the cell without the aryl radical being cleaved off.

This relates in particular to methods in which the cell is a eukaryotic or prokaryotic cell, for example a bacterial cell, yeast cell or a mammalian cell, preferably a human cell. In particular embodiments, the cell is a pathologically modified cell, for example a tumor cell.

The improved cellular uptake of the conjugates was not only observed in cells of mammals, but has also been demonstrated for other eukaryotes and even prokaryotes.

The conjugates, according to the invention, were examined microscopically for uptake into living cells. Initially, the FDA-labeled oligonucleotides were examined for the ability of CO_1 and CO_3 to enter cells. The corresponding fluorescein-labeled oligonucleotides CO_2 and CO_4 were used as compounds known from the prior art. All vital animal cell cultures studied took up the CO_1 and CO_3 (FDA-conjugates) within 5 to 10 minutes, whereas it was not possible to detect CO_2 and CO_4 (fluorescein conjugates) after this time in vital cells (Table 1).

Even though uptake into bacteria and yeast is considerably slower than in mammalian cells, some of the cells had taken up the oligonucleotides according to the invention after a period of two hours, whereas the normal fluorescein-labeled oligonucleotides were not taken up under these conditions. It is surprising that, in principle, all organisms which have hitherto been studied have taken up the oligonucleotides according to the invention better than known oligonucleotide derivatives. These organisms include, inter alia, animal cells, flagellates, yeasts, fungi, and bacteria (Table 3).

Furthermore, it has been found that cancer cells take up the oligonucleotides particularly well. The use of the oligonucleotides according to the invention is therefore particularly suitable for tumor therapy. The FDA-labeled antisense oligonucleotide CO_1, which is directed against eg5, inhibited proliferation of A549 cells simply when it was added to the medium, whereas the corresponding unmodified antisense oligonucleotide ON 1 and the fluorescein-labeled oligonucleotide CO_2 inhibited proliferation of the cancer cells only after fomulation with penetration enhancers such as CellFectin.

The invention relates to the use of conjugates in which the molecule to be transported is an oligonucleotide for hybridization with single-strand and/or double-strand nucleic acids, for example DNA (e.g., genes, cDNA) and/or RNA (e.g., pre-mRNA, mRNA). These conjugates can also bind with sequence-specificity to intracellular proteins, such as enzymes, for example polymerases or telomerases, or to transcription factors. The invention furthermore relates to the use of such conjugates for modulating and for completely or partially inhibiting the expression of certain target genes, for example for the complete or partial inhibition of transcription and/or translation. The invention also relates to the use of such conjugates as antisense oligonucleotides, ribozymes, sense oligonucleotides, triple helix-forming oligonucleotides, chimeroblasts, and/or decoy oligonucleotides. In addition, these conjugates can be used as auxiliaries in molecular biology.

The invention furthermore relates to the use of the oligonucleotides as medicaments and/or diagnostic aids and the use of the oligonucleotides for preparing medicaments and/or diagnostic aids. In particular, the oligonucleotides can be employed in medicaments for the prevention and/or treatment of diseases associated with the expression or overexpression of certain genes. Furthermore, the oligonucleotides can be used to diagnose such diseases, or to detect them early. Since the ability of the oligonucleotides according to the invention to enter cells is very good, they can be used for in vivo diagnosis, for example for in situ hybridization in entire organs or the intact organism.

The invention also provides medicaments, which comprise one or more conjugates according to the invention. The invention also provides a diagnostic aid, which comprises one or more conjugates according to the invention. The invention also provides a test kit, which comprises one or more conjugates according to the invention.

The invention also relates to the use of the oligonucleotides for the detection, separation and amplification of nucleic acids and analogs thereof. The conjugates are particularly suitable for detecting nucleic acids in cells, in particular in living cells. These cells can be of human or animal origin. The conjugates are also particularly suitable for the organisms listed in Table 3, in particular for the detection of pathogenic organisms. The oligonucleotides according to the invention can be used in known technical variations of the amplification of nucleic acids, in particular in LMPCR (ligation-mediated polymerase chain reaction), in the "Invader Assay"® (Third Wave Technologies, Inc., Wisconsin), in the TAQMAN SYSTEM® and in multiplex genotyping. Also advantageous is the use of the oligonucleotides for amplifying nucleic acids with the aid of the light-cycler, which allows a determination of the amplification in real time. Detection by the principle of molecular "beacons" in which the fluorescent dye does not fluoresce when it is not bound, because it is quenched by a second group in the oligomer, is a further possibility of using the oligonucleotides according to the invention. It is possible, for example, to combine an FDA derivative (for example at the 5'-end of the oligonucleotide) with a Dabcyl radical (for example conjugated at the 3'-end) which quenches the fluorescence signal in the unbound state even after conversion of the FDA derivative into the fluorescein derivative. These FDA-modified beacons would emit a fluorescence signal only after uptake into the cell and hybridization with the target mRNA.

The invention also relates to the use of the oligonucleotides or of medicaments comprising these oligonucleotides for treating diseases caused by or associated with overexpression of defined genes. The medicaments of the present invention can be used, for example, for treating disorders caused by viruses, for example by CMV, HIV, HSV-1, HSV-2, influenza, VSV, hepatitis B, or papilloma viruses. The medicaments of the present invention are also suitable, for example, for treating cancer. The medicaments of the present invention are furthermore suitable, for example, for treating disorders affected by integrins or cell-cell adhesion receptors, for example by VLA-4, VLA-2, ICAM, VCAM or ELAM. The medicaments of the present invention are also suitable, for example, for preventing restenosis, for the treatment of vitiligo and other depigmentation diseases or depigmentation disorders (for example of the skin, hairs, eyes), for example albinism and psoriasis, and of asthma.

The medicaments relate, for example, to pharmaceutical preparations which can be administered a) orally, for example in the form of tablets, sugar-coated tablets, hard or soft gelatin capsules, solutions, emulsions or suspensions, b) rectally, for example in the form of suppositories, or c) parenterally, for example in the form of solutions for injection. For preparing the medicaments, the conjugates can be processed, for example, in therapeutically inert organic and/or inorganic carriers; suitable carriers for tablets, sugar-coated tablets and hard gelatin capsules are, for example, lactose, corn starch or derivatives thereof, tallow and steric acid or salts thereof. Suitable carriers for solutions are water, polyols, sucrose, inverted sugar, and glucose, for solutions for injection are water, alcohols, polyols, glycerol and vegetable oils, for suppositories are vegetable and hydrogenated oils, waxes, fats, and semi-liquid polyols. The medicaments may furthermore comprise preservatives, solvents, stabilizers, wetting agents, emulsifiers, sweeteners, colorants, flavors, salts for altering the osmotic pressure, buffers, coating agents, antioxidants, and, if appropriate, other therapeutically active compounds. The medicaments are preferably applied topically or locally, such as, for example, with the aid of a catheter, or inhalated, or administered by injections or infusions. For injections, the conjugate is formulated in a liquid solution, preferably a physiologically acceptable buffer, such as, for example, Hank's solution or Ringer's solution. However, the conjugate can also be formulated in solid form and be dissolved or suspended prior to use. The dosages, which are preferred for systemic administration, are from approximately 0.01 mg/kg to approximately 50 mg/kg of body weight per day.

The conjugates, and/or their physiologically acceptable salts, can be administered as medicaments to animals, preferably mammals, and in particular humans, on their own, in mixtures with one another, or in the form of pharmaceutical preparations, which permit topical, percutaneous, parenteral, or enteral use and which comprise, as active component, an effective dose of at least one conjugate, in addition to customary pharmaceutically acceptable carriers and additives. The preparations usually comprise approximately 0.1 to 90% by weight of the therapeutically active compound. For the treatment of skin diseases, such as, for example, psoriasis or vitiligo, preference is given to topical use, for example in the form of ointments, lotions or tinctures, emulsions, suspensions. The medicaments are prepared in a manner known per se (for example Remingtons Pharmaceutical Sciences, Mack Publ. Co., Easton, Pa.), using pharmaceutically inert inorganic and/or organic carriers. For the preparation of pills, tablets, sugar-coated tablets and hard gelatin capsules, it is possible to use, for example, lactose, corn starch and/or derivatives thereof, talc, stearic acid and/or salts thereof, etc. Suitable carriers for soft gelatin capsules and/or suppositories are, for example, fats, waxes, semi-solid and liquid polyols, natural and/or hydrogenated oils, etc. Suitable carriers for the preparation of solutions and/or syrups are, for example, water, sucrose, inverted sugar, glucose, polyols, etc. Suitable carriers for the preparation of injections for solutions are water, alcohols, glycerol, polyols, vegetable oils, etc. Suitable carriers for microcapsules, implants, and/or rods are mixed polymers of glycolic acid and lactic acid. Furthermore suitable are liposome formulations known to the person skilled in the art (N. Weiner, Drug Develop Ind Pharm 15 (1989) 1523; "Liposome Dermatics, Springer Verlag 1992), for example HVJ liposomes (Hayashi, Gene Therapy 3 (1996) 878).

In addition to the active compounds and carriers, a medicament may also comprise additives, such as, for example, fillers, extenders, disintegrants, binding agents, lubricants, wetting agents, stabilizers, emulsifiers, preservatives, sweeteners, colorants, flavorings or aromatizers, thickening agents, diluents, buffer substances, furthermore solvents and/or solubilizers and/or agents for achieving a depot effect, and salts for changing the osmotic pressure, coating agents and/or antioxidants. They may also comprise two or more different oligonucleotides and/or their physiologically acceptable salts and furthermore, in addition to at least one oligonucleotide, one or more other therapeutically active substances. The dose may vary within wide limits and has in each case to be adjusted to the individual circumstances.

EXAMPLES

Example 1

Oligonucleotide Synthesis

Oligonucleotides were synthesized on an automatic DNA synthesizer (Applied Biosystems Model 380B or 394) using the standard phosphoramidite chemistry and oxidation with iodine (F. Eckstein, Ed "Oligonucleotides and Analogues, A Practical Approach", IRL Press, Oxford, 1991). For the introduction of phosphorothioate bridges in mixed phosphorothioates and phosphodiester oligonucleotides, oxidation was carried out using TETD (tetraethylthiuram disulfide) or Beaucage's reagent instead of iodine. After cleavage from the solid carrier (CPG or Tentagel) and removal of the protective groups with conc. $NH_3$ at 55° C. over a period of 18 h, the oligonucleotides were initially purified by precipitation with butanol (Sawadogo, Van Dyke, Nucl. Acids Res. 19:674 (1991)). The oligonucleotides were purified by preparative gel electrophoresis or FPLC. The sodium salt was then obtained by precipitation from a 0.5 M NaCl solution using 2.5 parts by volume of ethanol.

The oligonucleotides were analyzed by
a) analytic gel electrophoresis in 20% acrylamide, 8 M urea, 454 M Trisborate buffer, pH 7.0 and/or
b) HPLC analysis: Waters GenPak FAX, gradient $CH_3CN$ (400 ml), $H_2O$ (1.61), $NaH_2PO_4$ (3.1 g), NaCl (11.7 g), pH 6.8 (0.1 M of NaCl) to $CH_3CN$ (400 ml), $H_2O$ (1.61), $NaH_2PO_4$ (3.1 g), NaCl (175.3 g), pH 6.8 (1.5 M of NaCl) and/or
c) capillary gel electrophoresis Beckmann capillary eCAP™, U100P gel column, length 65 cm, I.D. 100 mm, window 15 cm from one end, buffer 140 µM Tris, 360 mM boric acid, 7 M urea and/or
d) electrospray mass spectroscopy The analysis of the oligonucleotide showed that the latter was in each case present in a purity of greater than 90% and in most cases greater than 95%.

Example 2

Introduction of a 5'-Amino-Linker into an Oligonucleotide

The oligonucleotide was synthesized as described in Example 1. After coupling of the last nucleotide, the dimethoxytrityl group at the 5'-end was cleaved off. The free hydroxyl group was reacted with the commercially available 5'-amino-modifier C6 (from Eurogentic, Seraing, Belgium) under tetrazole catalysis and oxidized with iodine water. The oligonucleotide was then cleaved off from the carrier by treatment with conc. ammonia at 50° C. overnight, and all base-labile protective groups at the internucleoside groups and the amino functions of the heterocyclic bases were cleaved off. In the last step, the monomethoxytrityl protective group was cleaved off by treatment with 80% strength acetic acid at ambient temperature for 3 hours. The resulting oligonucleotide was analyzed as described in Example 1.

Example 3

Conjugation of the Amino-Linker Oligonucleotide with FDA Isothiocyanate

10 OD (260) units of the 5'-amino-linker oligonucleotide from Example 2 were dissolved in 16 µl of 0.2 M triethylammonium bicarbonate (TBK) buffer and admixed with 125 µl of dimethylformamide (DMF). 1.5 mg of FDA isothiocyanate was added to this mixture, and the mixture was then shaken for 3 hours under exclusion of light. The result of the reaction was checked by HPLC. 2 µl of conc. acetic acid was then added, and the mixture was concentrated under reduced pressure. The product was then purified by precipitation with butanol. The correct molecular weight was determined by ESI mass spectroscopy. To avoid hydrolysis of the aromatic ester, the samples were always kept at a pH below 7.

Example 4

Synthesis of CO_1
(5'-F3-G*CGAC*GC*CAT*GAC*G*G-3';
F3=FDA)

The oligonucleotide was synthesized as described in Example 1 starting from a CPG carrier which had 1 µmol of deoxyguanosine attached via the 3'-end. The positions marked with * were oxidized with Beaucage reagent to introduce a phosphorothioate bridge. Coupling with the 5'-amino-modified C6 was then carried out as described in Example 2. Deprotection with conc. ammonia and 80% acetic acid gave 96 OD (260) units of the 5'-amino-linker-G*CGAC*GC*CAT*GAC*G*G-3'.

10 OD (260) units of the 5'-amino-linker oligonucleotide were then reacted with FDA isothiocyanate as described in Example 3. Precipitation with butanol gave 8.4 OD (260) units of the desired FDA-labeled oligonucleotide. ESI-MS for the di-Na salt: 5395.93 (calculated for di-Na: 5395.09).

Example 5

Synthesis of CO_13 (5'-F3-TATTCCGTCAT-3')

The oligonucleotide was synthesized as described in Example 1 starting from a CPG carrier, which had 1 µmol of thymidine attached via the 3'-end. All oxidations were carried out using iodine water. Coupling with the 5'-amino-modifier C6 was then carried out as described in Example 2. Deprotection with conc. ammonia and 80% acetic acid gave 72 OD (260) units of the 5'-amino-linker-TATTCCGTCAT-3'. Purification over a preparative polyacrylamide gel gave 43 OD (260) units.

10 OD (260) units of the 5'-amino-linker oligonucleotide were then reacted with FDA isothiocyanate as described in Example 3. Precipitation with butanol gave 9.1 OD (260) units of the desired FDA-labeled oligonucleotide. ESI-MS: 3934.1 (calculated MW 3933.8).

Example 6

Synthesis of CO_21 (5'-F7-A*T*G A C*G G A A*T*T*C)

The oligonucleotide was synthesized as described in Example 1 starting from a CPG carrier, which had 1 μmol of N6-benzoylcytidine attached via the 3'-end. All oxidations were carried out using iodine water. Coupling with the 5'-amino-modifier C6 was then carried out as described in Example 2. Deprotection with conc. ammonia and 80% acetic acid gave 145 OD (260) of the 5'-amino-linker-A*T*G A C*G G A A*T*T*C-3'.

10 OD (260) units of the 5'-amino-linker oligonucleotide were dissolved in 16 μl of 0.2 M TBK buffer and 95 μl of DMF, and the mixture was reacted with 30 μl of the activated ester of p-acetoxybenzoic acid, which had been prepared beforehand. The activated ester was prepared by mixing 50 μl of 0.2 M p-acetoxybenzoic acid with 50 μl of 0.3 M TBTU, in each case in DMF, followed by a one-hour reaction at ambient temperature. After a 4-hour reaction of the amino-linker-oligonucleotide with the activated ester, 2 μl of semi-concentrated acetic acid was added, and the mixture was concentrated under reduced pressure. Excess reagent was removed by precipitation with butanol. This gave 10.7 OD (260) units of the desired oligonucleotide conjugate. ESI-MS: 4109.2 (calculated MW 4108.2).

Example 7

Examination of the Cellular Uptake of the Oligonucleotide Conjugates

To examine the cellular uptake, 1 ml of cell suspension was admixed in a Bachofer chamber in culture medium (or after rinsing in PBS in the case of media with inherent fluorescence) under microscopic control with 1 ml of a 1 pmolar solution of the oligonucleotide conjugate, mixing being carried out using the pipette, and by shaking the chamber. Microscopy was carried out with the aid of the Zeiss Axiovert 135 TV apparatus (100× Plan-Neofluar) in the phase-contrast mode. The fluorescence filters used were 09 (450-490/FT 510/LP 520)/HBO 59W filters. The reference used was a 2.4 μM solution of FDA (Aldrich Chem. Co., FW.416.39) in acetone/PBS buffer (1:1000; v:v). In the case of FDA conjugates, the inherent fluorescence of the fluorescein ligand formed by ester cleavage can be monitored after uptake. In the case of nonfluorescent ligands such as acetoxynaphthalenecarboxylic acid, a suitable fluorescence label (FITC, rhodamine, cyanine dye Dy3 or Dy5) was additionally attached to the oligonucleotide. A double-label as in CO_9 served to demonstrate that FDA was not cleaved off from the oligonucleotide. The individual samples were evaluated 2 to 120 minutes after addition of the oligonucleotide conjugate. In the case of REH cells, fluorescence was clearly evident after 5 to 10 min, in the case of K562 and adherent cells and also insect cells, there was a certain increase right up to 60 min after addition. In the case of free-living protozoa, the uptake took up to 1 h. In the case of yeasts, uptake occurred only after a prolonged period of time and was not homogeneous in all cells. The uptake of FDA oligonucleotide conjugates into fungal spores was better than into hyphen cells. The results are summarized in Tables 1 to 3.

Example 8

Examination of the Antiproliferative Action of the Oligonucleotide Conjugates

The REH cells (human pre-B cell leukemia, DSM ACC 22) or A549 tumor cells were cultured in OptiMEM with 10% fetal calf serum (FCS; GIBCO-BRL) at 37° C. under 5% $CO_2$. On the day prior to the experiment, the cells were subcultured for about 24 hr to a cell concentration of approximately $1 \times 10^6$/ml. The oligonucleotides or their conjugates were dissolved in distilled water to give 1 mM stock solutions and stored at −20° C. The cells were sown into 24-well plates ($1 \times 10^6$ cells/ml in OptiMEM with 10% FCS). For the examination, the oligonucleotide derivatives were diluted to 2 μM (in OptiMEM without FCS). 100 μl/well of oligonucleotide solution and 100 μl/well of cell suspension were mixed (total volume 200 μl/well; oligonucleotide concentration 1 μM, serum concentration 5% FCS, cell concentration $0.5 \times 10^6$ cells/ml). After 4 h of incubation at 37° C. and 5% $CO_2$, 800 μl of OptiMEM with 11% FCS were added per well (cell concentration now $1 \times 10^5$ cells/ml, serum concentration now 10% FCS), and the incubation was continued. After 96 h at 37° C. and 5% $CO_2$, the cell concentration was measured using a Casy 1 (from Scharfe). To this end, the cells in each well were mixed by being sucked into a 1000-μl pipette and blown out again, in each case 10 times, and diluted immediately 1:100 (in the case of stronger cell growth 1:200) with Casyton. The mean value of the cell density was determined in each case from 3 identical samples of a batch.

Example 9

Synthesis of 5'-F4'(CO—NH)-A*T*G A C*G G A A*T*T*C

The oligonucleotide was synthesized as described in Example 1 starting from a CPG carrier, which had 1 μmol of N-benzoylcytidine attached via the 3'-end. To introduce a phosphorothioate radical (if * is present in the sequence), the oxidations were carried out using iodine water or Beaucage reagent. Coupling with the 5'-amino-modifier C6 was then carried out as described in Example 2. Deprotection with conc. ammonia and 80% acetic acid gave 145 OD (260) of the 5'-amino-linker-A*T*G A C*G G A A*T*T*C-3'.

10 OD (260) units of the 5'-amino-linker-oligonucleotide were dissolved in 16 μl of 0.2 M TBK buffer and 95 μl of DMF, and the mixture was reacted with 12.5 μl of dichlorofluorescein diacetate hydroxysuccinimide (MW: 626.36). After a 3-hour reaction of the amino-linker-oligonucleotide with the hydroxysuccinimide, 2 μl of semi-concentrated acetic acid are added, and the mixture is concentrated under reduced pressure. After desalting over a NAP® column (Pharmacia), a precipitation with butanol was carried out. This gave 2.8 OD (260) units of the desired oligonucleotide dichlorofluorescein diacetate conjugate. ESI-MS: 4403.3 (calculated MW 4403.2).

Example 10

Synthesis of 5'-F2'-(CO—NH)-A*T*G A C*G G A A*T*T*C

The 5'-amino-linker-A*T*G A C*G G A A*T*T*C-3' oligomer was prepared as described in Example 9. 10 OD (260) units of the 5'-amino-linker-oligonucleotide were dissolved in 16 µl of 0.2 M TBK buffer and 95 µl of DMF, and the mixture was reacted with 12.5 µl of carboxyfluorescein dipivalate hydroxysuccinimide (MW:641.64). After a 2-hour reaction of the amino-linker-oligonucleotide with the hydroxysuccinimide, another 12.5 µl of the hydroxysuccinimide are added, and the reaction is continued for a further 2 hours. 2 µl of semi-concentrated acetic acid are then added and the mixture is concentrated under reduced pressure. Desalting over a NAP® column (Pharmacia) was followed by precipitation with butanol. This gave 8.1 OD (260) of the desired oligonucleotide fluorescein dipivalate conjugate. ESI-MS:4472.9 (calculated MW 4471.6).

Example 11

Synthesis of 5'-F9-A*T*G A C*G G A A*T*T*C

The 5'-amino-linker-A*T*G A C*G G A A*T*T*C-3' oligomer was prepared as described in Example 9. 10 OD (260) units of the 5'-amino-linker-oligonucleotide were dissolved in 16 µl of 0.2 M TBK buffer and 95 µl of DMF, and the mixture was reacted with 25 µl of the activated ester of acetoxynaphthylcarboxylic acid. The activated ester was prepared by mixing 12.5 µl of 0.2 M acetoxynaphthylcarboxylic acid (2.5 mg in 50 µl of DMF) with 12.5 µl of TBTU (4 mg in 50 µl of DMF), followed by a one-hour reaction at ambient temperature. After a 17-hour reaction of the amino-linker-oligonucleotide with the activated ester, 2 µl of semi-concentrated acetic acid was added, and the mixture was concentrated under reduced pressure over a NAP® column (Pharmacia) was followed by precipitation with butanol. This gave 8.5 OD (260) units of the desired oligonucleotide acetoxynaphthyl conjugate. ESI-MS: 4158.2 (calculated MW 4157.2).

Example 12

Synthesis of 5'-F8-A*T*G A C*G G A A*T*T*C

The 5'-amino-linker-A*T*G A C*G G A A*T*T*C-3' oligomer was prepared as described in Example 9.10 OD (260) units of the 5'-amino-linker-oligonucleotide were dissolved in 16 µl of 0.2 M TBK buffer and 95 µl of DMF, and the mixture was reacted with 25 µl of the activated ester of acetoxycoumarincarboxylic acid. The activated ester was prepared by mixing 12.5 µl of 0.2 M acetoxycoumarincarboxylic acid (2.7 mg in 50 µl of DMF) with 12.5 µl of TBTU (4 mg in 50 µl of DMF), followed by a one-hour reaction at ambient temperature. After a 17-hour reaction of the amino-linker-oligonucleotide with the activated ester, 2 µl of semi-concentrated acetic acid are then added, and the mixture is concentrated under reduced pressure. Desalting over over a NAP® column (Pharmacia) was followed by precipitation with butanol. This gave 8.0 OD (260) units of the desired oligonucleotide acetoxycoumarine conjugate. ESI-MS: 4178.5 (calculated MW 4175.2).

Example 13

Synthesis of 5'-F3-(dA)$_n$dA*dA*dA (n=17, 47 and 77; F3=FDA)

The oligonucleotides were synthesized as described in Example 1 starting from a CPG carrier which was derivatized with N6-benzoyl-2'-deoxyadenosine via the 3'-end. The oxidations after the first two couplings were carried out using Beaucage reagent to introduce the phosphorothioate radicals (marked in the sequence by *), all other oxidations were carried out using iodine water. Coupling with the 5'-amino-modifier C6 was then carried out as described in Example 2. Deprotection with conc. ammonia and 80% acetic acid and purification over a preparative polyacrylamide gel gave 2.95 OD (260) of the 5'-amino-linker-(dA)$_{17}$dA*dA*dA, 4.9 OD (260) of the 5'-amino-linker-(dA)$_{47}$dA*dA*dA and 5 OD (260) of the 5'-amino-linker-(dA)$_{77}$dA*dA*dA. In each case, the 5'-amino-linker-oligonucleotides were dissolved in 8 µl of 0.2 M TBK buffer and 62 µl of DMF, and the mixture was reacted with 1.6 µl of FDA isothiocyanate. After a 3-hour reaction, further FDA isothiocyanate is added, and the reaction is continued for 2 hours. 2 µl of semi-concentrated acetic acid are then added and the mixture is concentrated under reduced pressure. Desalting over over a NAP® column (Pharmacia) was followed by precipitation with butanol. This gave 1.5 OD (260) units of 5'-F3-(dA)$_{77}$dA*dA*dA, 2.2 OD (260) units of 5'-F3-(dA)$_{47}$dA*dA*dA and 0.9 OD (260) units of 5'-F3-(dA)$_{77}$dA*dA*dA.

Example 14

Synthesis of the Doubly Labeled Oligonucleotide 5'-Cy3-A*T*G A C*G G A A*T*T*C-C6-F3; F3=FDA The oligonucleotide was synthesized as described in Example 1 starting from a CPG carrier which allows the introduction of a C6-amino-linker at the 3'-end (Petrie et al. *Bioconjugate Chem.* 3:85-87 (1992)). The oxidations were carried out using iodine water or Beaucage reagent to introduce a phosphorothioate radical (if * is present in the sequence). After the last dimethoxytrityl protective group had been cleaved off, the 5'-end of the oligonucleotide was reacted with a Cy3-CE phosphoramidite (from Glen Research, Sterlin, Va.; Catalog No. 10-5913-xx) and oxidized with iodine water. Deprotection with conc. ammonia (2 hours at 70° C.) gave 64 OD (260) units of the crude product. Purification over a preparative polyacrylamide gel gives 3.8 OD of the 5'-Cy3-A*T*G A C*G G A A*T*T*C-C6-amino-linker-3', 3.5 OD (260) units of which are dissolved in 8 µl of 0.2 M TBK buffer and 62 µl of DMF, and reacted with 1.6 µmol of FDA isothiocyanate. After a 3.5-hour reaction of the amino-linker-oligonucleotide with the hydroxysuccinimide, 1 µl of semi-concentrated acetic acid is added and the mixture is concentrated under reduced pressure. Desalting over a NAP® column (Pharmacia) was followed by precipitation with butanol. This gave 3.5 OD (260) units of the desired doubly-labeled oligonucleotide 5'-Cy3-A*T*G A C*G G A A*T*T*C-C6-F3. ESI-MS: 4926.2 (calculated MW 4927.1).

Example 15

Synthesis of 5'-F3-A*T*G A C*G G A A*T*T*C; F3-FDA

The 5'-amino-linker-A*T*G A C*G G A A*T*T*C-3' oligomer was prepared as described in Example 9. 10 OD (260)

units of the 5'-amino-linker-oligonucleotide were dissolved in 16 µl of 0.2 M TBK buffer and 95 µl of DMF, and the mixture was reacted with 25 µl of FDA isothiocyanate (5 mg in 100 µl DMF). After a 3-hour reaction of the amino-linker-oligonucleotide with the isothiocyanate, another 5 µl of the isothiocyanate are added, and the reaction is allowed to continue for another 2 hours. 2 µl of semi-concentrated acetic acid are then added, and the mixture is concentrated under reduced pressure. Desalting over a NAP® column (Pharmacia) was followed by precipitation with butanol. This gave 8.5 OD (260) units of the desired oligonucleotide fluorescein diacetate conjugate. ESI-MS: 4418.4 (calculated MW 4418.5).

Example 16

Comparison of the Cellular Uptake of Oligonucleotide Conjugates of Different Lengths 5'-F3-(dA)$_n$ dA*dA*dA (n=17, 47 and 77; F3=FDA)

The cellular uptake of the conjugates of different length and molecular weight from Example 13 was carried out in principle as described in Example 7, using REH cells. Quantification was carried out with the aid of a flow cytometer. After 60 minutes, the relative fluorescence signal for 5'-F3 (dA)$_{17}$dA*dA*dA ("A20") is 49, that for 5'-F3(dA)$_{47}$ dA*dA*dA ("A50") is 34 and that for 5'-F3-(dA)$_{77}$ dA*dA*dA (n"A80") is 91. Surprisingly, the uptake of the FDA conjugate with the greatest oligonucleotide moiety, comprising a total of 80 nucleotides, was taken up most effectively by the REH cells.

Example 17

Comparison of the Cellular Uptake of Oligonucleotide Conjugates with Different Derivatization Fluorescein dipivalate is a compound related to fluorescein diacetate (FDA) which has an increased stability of the ester groups. The corresponding oligonucleotide conjugates were examined for uptake using a flow cytometer. The increased stability of the pivalate to alkali and esterases results in a reduced uptake of the corresponding oligonucleotide conjugate. Thus, the relative fluorescence measured for the fluorescein diacetate conjugate after 60 minutes is 195, whereas it is only 55 for the corresponding fluorescein dipivalate conjugate.

Example 18

Examination of the Cellular Uptake of the Doubly-Labeled Oligonucleotide Conjugate 5'-Cy3-A*T*G A C*G G A A*T*T*C-C6-FDA from Example 13

The FACScan showed that the Cy3 oligonucleotide F3 conjugate is rapidly taken up by REH cells. Treatment of the cells with an oligonucleotide conjugate/Cellfectin complex gives a similar, but considerably less uniform, uptake. The effect of the FDA conjugate interferes considerably with that of the Cellfectin oligonucleotide complex.

Figure 9:
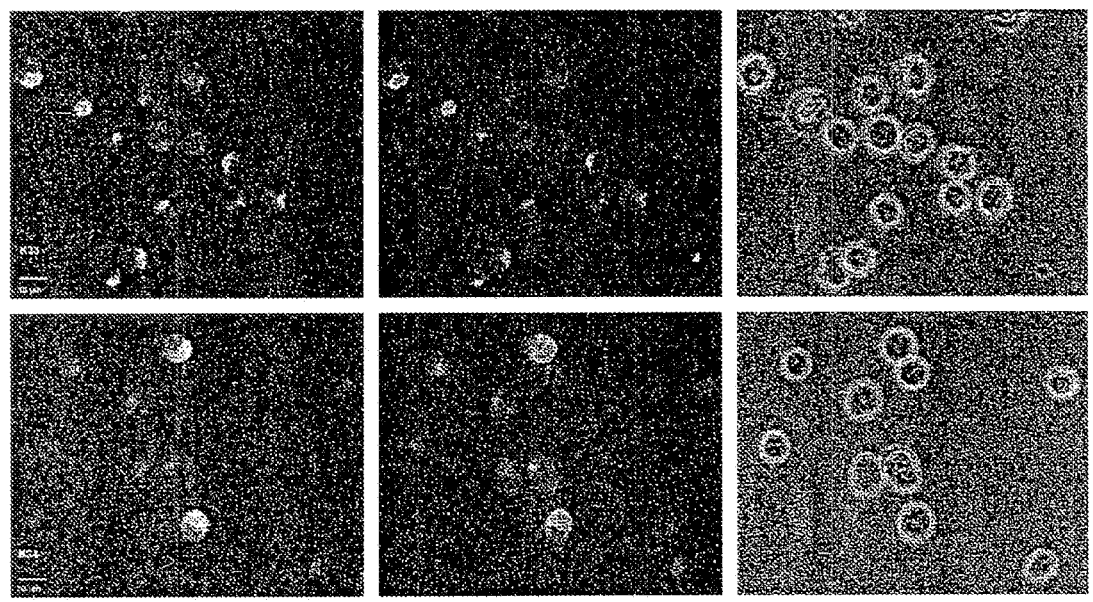
FIG. 9: Examination of the uptake of doubly labeled Cy3 oligonucleotide F3 conjugate (1 µM) during incubation with REH cells by fluorescence microscopy. Uptake after 4 hours. Left: Fluorescence; Middle: Cyanim dye; Right: Phase Contract Microscopy; Obove: Oligonucleotide K33; Underneath: Oligonucleotide K34.

Also to be examined was the colocalization of the two different marker groups on the oligonucleotide in the incubation with cells, to exclude the possibility that the measured fluorescence was based only on the cleaved FDA or fluorescein. The Cy3 oligonucleotide F3 conjugate had the cyanine dye covalently attached to the 5'-end and the FDA covalently attached to the 3'-end. FIG. 9 shows the green and red fluorescence after a 4-hour incubation of the REH cells with the Cy3 oligonucleotide F3 conjugate. Since colocalization of the two markers in the cells can be observed, it has to be assumed that the oligonucleotide is taken up in intact form. Only the acetyl groups of the FDA moiety were hydrolyzed, presumably by esterases, because the nonfluorescent FDA radical was evidently converted into the fluorescent fluorescein radical. Uptake of the Cy3/FDA conjugate was very rapid, since the two markers could be detected after only 7 minutes after addition.

Four concentrations of the oligonucleotide FDA conjugate CO_1 from Example 4 were examined for antiproliferative activity in A549 tumor cells. The conjugate inhibited the proliferation without addition of a penetration enhancer. The corresponding oligonucleotide without F3 conjugate (ON1) inhibits proliferation only after complex formation with a penetration enhancer (CellFectin, from Gibco-BRL). The results are shown in Table 4.

TABLE 1

Examination by fluorescence microscopy of the uptake of FDA-labeled oligonucleotides (conjugate oligonucleotide-FDA) into mammalian cells.

| Mammalian cells: name of the cell line | Fluorescence after 5 min | | Fluorescence after 20 min | | Fluorescence after 60 min | | Fluorescence after 120 min | |
|---|---|---|---|---|---|---|---|---|
| | A | B | A | B | A | B | A | B |
| REH | + | − | + | − | ++ | − | ++ | * |
| K562 | | | (+) | | + | | + | |
| Lu 18 | | | | | (+) | | + | |
| KB3-1 | | | | | + | | + | |
| Ptk2 | | | | | (+) | | + | |

A: Incubation with FDA-labeled oligonucleotides CO_1 and CO_3
B: Incubation with fluorescein-labeled oligonucleotides CO_2 and CO_4
(+) weak uptake
+ moderate uptake
++ very strong uptake
− no uptake
* uptake only into damaged cells

TABLE 2

Examination by fluorescence microscopy of the uptake of FDA-labeled oligonucleotides into insect cells (for the legend, see Table 1).

| Insect cells | Fluorescence after 20 min | | Fluorescence after 60 min | | Fluorescence after 120 min | |
|---|---|---|---|---|---|---|
| | A | B | A | B | A | B |
| SF9 cells | + | − | ++ | − | ++ | − |

TABLE 3

Examination by fluorescence microscopy of the uptake of FDA-labeled oligonucleotides into various organisms.

| Organism | Fluorescence after 20 min | | Fluorescence after 60 min | | Fluorescence after 120 min | |
|---|---|---|---|---|---|---|
| | A | B | A | B | A | B |
| *Bac. subtilis* (6633) # | − | − | − | − | + | − |
| *L. bulgaricus* # | − | − | + | − | + | − |
| *E. coli* (K12) # | − | − | + | − | + | − |
| *Yarrowia lipolytica* # (wild form H 222) | − | − | − | − | + | − |
| *Sacchromyces cerevisiae* # | − | − | − | − | + | − |
| *Fusarium culmorum* spores (JP15, fungus) | (+) | − | + | − | + | − |
| *Reticulomyxa filosa* cysts (sweet water ameba) | − | − | ++ in particular nuclei | − | ++ | − |
| *Haematococcus pluvialis* (green algae, flagellate) | − | − | + | − | + | − |
| *Chlorogonium* sp. (green algae, flagellate) | − | − | + | − | + | − |
| *Dunaliella salina* (sea diatome) | − | − | + | − | + | − |

A: Incubation with FDA-labeled oligonucleotides CO_1 and CO_3
B: Incubation with fluorescein-labeled oligonucleotides CO_2 and CO_4
(for the legend for the evaluation, see Table 1)
was only taken up into some of the cells of these rapidly dividing organisms

TABLE 4

Results from Example 8.

| Substance | Cell density | % inhibition |
|---|---|---|
| none | 5.96 | — |
| FDA | 6.05 | −1.5 |
| 100 nM CO_1 | 5.65 | 5.2 |
| 200 nM CO_1 | 5.3 | 11.1 |
| 500 nM CO_1 | 5.03 | 15.6 |
| 1000 nM CO_1 | 4.16 | 30.2 |

TABLE 5

Transfection of FDA conjugates (A20, A50, A80 from Example 15) as a function of the length

| Time (min) | Fluorescence A20 | Fluorescence A50 | Fluorescence A80 |
|---|---|---|---|
| 0 | 0.0103 | 0.0103 | 0.0103 |
| 10 | 11.71 | 8.9 | 43.31 |
| 20 | 39.68 | 28.06 | 88.36 |
| 30 | 48.59 | 34.38 | 91.28 |
| 40 | 54.7 | 38.75 | 92.35 |
| 50 | 58.66 | 41.64 | 93.19 |
| 60 | 62.13 | 44.33 | 93.62 |

TABLE 6

Figure 8:
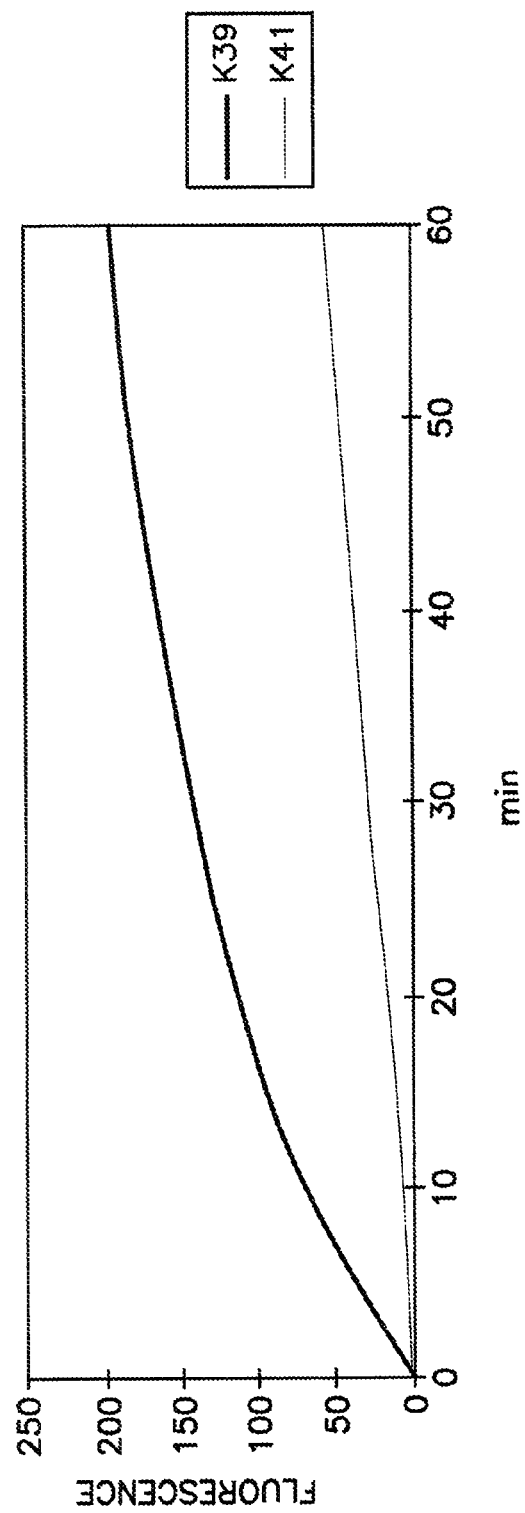
FIG. 8: Comparison of the uptake of fluorescein diacetate and fluorescein dipivalate oligonucleotide conjugates into the cell
  K39: carboxyfluorescein diacetate (F3 equals FDS) from Example 15
  K41: carboxyfluorescein dipivalate (F2) from Example 10

Comparison of the cellular uptake of fluorescein diacetate and fluorescein dipivalate oligonucleotide conjugates (Example 16, FIG. 8).

| Time (min) | Fluorescence K39 | Fluorescence K41 |
|---|---|---|
| 0 | 2.66 | 2.75 |
| 10 | 72.37 | 8.49 |
| 20 | 112.34 | 18.17 |
| 30 | 142.97 | 28.67 |
| 40 | 164.64 | 38.34 |
| 50 | 184.96 | 46.62 |
| 60 | 195.57 | 55.26 |
| 70 | | |
| 80 | 218.12 | 68.02 |
| 90 | | |
| 100 | 231.04 | 83.7 |
| 110 | | |
| 120 | 253.84 | 97 |

We claim:

1. A method for transporting an oligonucleotide across a membrane which comprises incubating a conjugate with the membrane, wherein the conjugate comprises the oligonucleotide attached to an aryl radical and has the following structure: 5'-F3-amino linker-phosphorothioate modified oligonucleotide with 12 or 15 nucleotides, wherein F3 is:

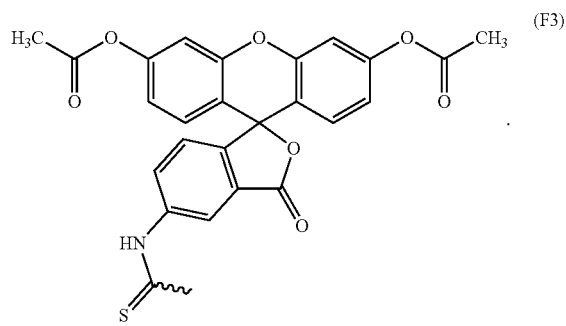

2. The method of claim 1, wherein the oligonucleotide has a length of 8 to 80 nucleotides.

3. A method for transporting an oligonucleotide into a cell which comprises incubating a conjugate with the cell, wherein the conjugate comprises an oligonucleotide attached to an aryl radical and has the following structure: 5"-F3-amino linker-phosphorothioate modified oligonucleotide with 12 or 15 nucleotides, wherein F3 is:

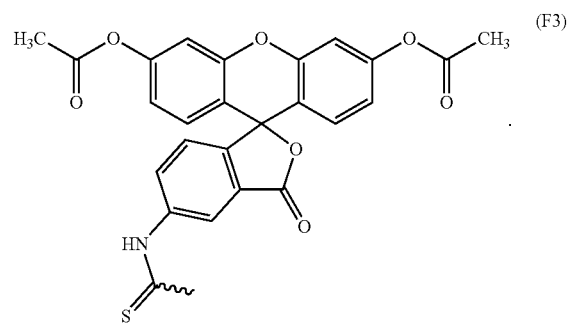

and the conjugate is transported into the cell without the aryl radical being cleaved off.

4. The method as claimed in claim 3, wherein the cell is a eukaryotic or a prokaryotic cell.

5. The method as claimed in claim 3, wherein the cell is a bacterial cell, yeast cell or a mammalian cell.

6. The method as clamed in claim 3, wherein the cell is a human.

7. The process as claimed in claim 3, wherein the cell is a tumor cell.

8. The method of claim 3, wherein the oligonucleotide has a length of 8 to 80 nucleotides.

* * * * *